United States Patent
Bazin-Lee et al.

(10) Patent No.: US 10,584,125 B2
(45) Date of Patent: Mar. 10, 2020

(54) ADENINE DERIVATIVES WHICH ARE USEFUL IN THE TREATMENT OF ALLERGIC DISEASES OR OTHER INFLAMMATORY CONDITIONS

(71) Applicant: GlaxoSmithKline Biologicals SA, Rixensart (BE)

(72) Inventors: Helene G. Bazin-Lee, Research Triangle Park, NC (US); Yufeng Li, Research Triangle Park, NC (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 214 days.

(21) Appl. No.: 15/526,345

(22) PCT Filed: Nov. 13, 2015

(86) PCT No.: PCT/IB2015/058774
§ 371 (c)(1),
(2) Date: May 12, 2017

(87) PCT Pub. No.: WO2016/075661
PCT Pub. Date: May 19, 2016

(65) Prior Publication Data
US 2018/0291026 A1    Oct. 11, 2018

Related U.S. Application Data

(60) Provisional application No. 62/079,027, filed on Nov. 13, 2014.

(51) Int. Cl.
| | | |
|---|---|---|
| A61K 31/522 | (2006.01) | |
| C07D 473/18 | (2006.01) | |
| A61K 31/52 | (2006.01) | |
| A61K 39/39 | (2006.01) | |
| A61K 39/00 | (2006.01) | |

(52) U.S. Cl.
CPC ............ C07D 473/18 (2013.01); A61K 31/52 (2013.01); A61K 31/522 (2013.01); A61K 39/39 (2013.01); *A61K 2039/55511* (2013.01)

(58) Field of Classification Search
CPC ............................ A61K 31/522; C07D 473/18
USPC ...................................... 514/263.22; 544/265
See application file for complete search history.

(56) References Cited

FOREIGN PATENT DOCUMENTS

| | | | |
|---|---|---|---|
| WO | 2010018134 A1 | 2/2010 | |
| WO | WO2010/018134 | * 2/2010 | ........... A61K 31/522 |
| WO | WO 2010/018134 A1 | 2/2010 | |
| WO | 2010048520 A1 | 4/2010 | |
| WO | 2011017611 A1 | 2/2011 | |

OTHER PUBLICATIONS

Bazen et al., Structural requirements for TLR7-selective signaling by 9-(4-piperidinylalkyl)-8-oxoadenine derivatives, Bioorganic & Medicinal Chemistry Letters, year 2015, pp. 1318-1323, vol. 25.
Smith et al., Evaluation of novel synthetic TLR7/8 agonists as vaccine adjuvants, Vaccine, year 2016, vol. 34, pp. 4304-4312.

* cited by examiner

*Primary Examiner* — Jeffrey H Murray
(74) *Attorney, Agent, or Firm* — Birch, Stewart, Kolasch & Birch, LLP

(57) ABSTRACT

Compounds of formula (I):

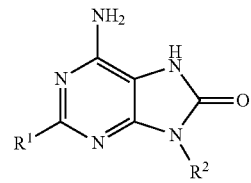

wherein: $R^1$ is butoxy or methylbutoxy; $R^2$ is a group having the structure:

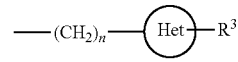

where n is an integer having a value of five; Het is a six-membered saturated heterocycle containing five carbon atoms and one nitrogen atom, wherein Het is attached to the —$(CH_2)_n$— moiety at the carbon 4 position of the heterocycle; and $R^3$ is hydrogen; or pharmaceutically acceptable salts thereof; and their use as vaccine adjuvants and in the treatment of various disorders.

6 Claims, 8 Drawing Sheets

| FIG. 1C | 3a | 3b | 3c | 3d | 3e | 3f | 3g |
|---|---|---|---|---|---|---|---|
| hTLR7 $EC_{50}$ (μM) | -- | 4.0 | 0.15 | 0.62 | 0.15 | 0.10 | 0.23 |
| hTLR8 $EC_{50}$ (μM) | -- | 1.8 | 231 | 260 | 131 | 57 | 29 |

ADENINE DERIVATIVES WHICH ARE USEFUL IN THE TREATMENT OF ALLERGIC DISEASES OR OTHER INFLAMMATORY CONDITIONS

CROSS-REFERENCE TO RELATED PATENTS AND PATENT APPLICATIONS

This application is a 371 of International Application No. PCT/IB2015/058774, filed 13 Nov. 2015, which claims the benefit of U.S. Provisional Application Ser. No. 62/079,027 filed Nov. 13, 2014.

STATEMENT REGARDING FEDERALLY SPONSORED RESEARCH

Aspects of this invention were made with United States government support pursuant to NIH Contract# HHSN272200900036C, the United States government may have certain rights in the invention.

BACKGROUND OF THE INVENTION

The present invention relates to compounds, processes for their preparation, compositions containing them, and their therapeutic use as vaccine adjuvants and in the treatment of various disorders.

The innate immune system recognises microbes via a limited number of germline-encoded Pattern-Recognition Receptors (PRRs) which have a number of important characteristics.

Toll-like receptors (TLR) are a family of structurally related PRRs that detect highly conserved microbial components common to large classes of pathogens. TLRs are expressed on immune cells and upon activation mobilize defense mechanisms aimed at eliminating the invading pathogens. Of the more than ten known TLRs that have been identified in humans, some appear to be restricted to cytoplasmic compartments and involved in the detection of non-self nucleic acids (TLRs 3, 7, 8, and 9). See, e.g., Akira et al., *Nat Rev Immunol* 2004, 4, 499-511; O'Neill, et al., *Nat Rev Immunol* 2013, 13, 453-460.

Activation of TLRs regulates intracellular signaling pathways leading to the expression of inflammatory cytokines/chemokines and type I interferons (IFNα/β), which can lead to the preferential enhancement of antigen-specific humoral and cell-mediated immune responses.

TLR7 and TLR8 are members of the subgroup of TLRs (TLRs 3, 7, 8, and 9) localised in the endosomal compartment of cells. TLR7 plays a key rôle in anti-viral defence via the recognition of ssRNA (Diebold S.S. et al, *Science*, 2004: 303, 1529-1531; and Lund J. M. et al, *PNAS*, 2004: 101, 5598-5603). TLR7 has a restricted expression-profile in human and is expressed predominantly by B cells and plasmacytoid dendritic cells (pDC), and to a lesser extent by monocytes. Plasmacytoid DCs are a unique population of lymphoid-derived dendritic cells (typically 0.2-0.8% of Peripheral Blood Mononuclear Cells (PBMCs)) and are the primary type I interferon-producing cells secreting high levels of interferon-alpha (IFNα) and interferon-beta (IFNβ) in response to viral infections (Liu Y-J, *Annu. Rev. Immunol.*, 2005: 23, 275-306).

Small-molecule agonists of TLR7 have been described which can induce cytokines in animals and in man (Takeda K. et al, *Annu. Rev. Immunol.*, 2003: 21, 335-76). TLR7 agonists include imidazoquinoline compounds such as imiquimod and resiquimod, oxoadenine analogues and also nucleoside analogues such as loxoribine and 7-thia-8-oxoguanosine, which are known to induce interferon alpha. International Patent Application publication number WO 2007/034882 (PCT/JP2006/318758; Dainippon Sumitomo Pharma Co. Ltd./AstraZeneca Aktiebolag) discloses certain adenine compounds identified as useful as medicine.

Certain adenine derivative compounds have been shown to be inducers of human interferon. Compounds which induce human interferon may be useful as vaccine adjuvants, as well as in the treatment of various disorders, including infectious diseases, asthma, cancer, inflammatory conditions, and allergic diseases. It is thus desirable to provide compounds having selectivity and/or potency for TLR7/8 and high relative cytokine induction.

SUMMARY OF THE INVENTION

In a first aspect, there is provided a compound of formula (I):

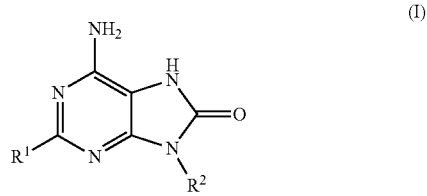

wherein;
$R^1$ is butoxy or methylbutoxy;
$R^2$ is a group having the structure:

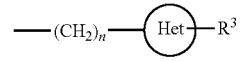

where n is an integer having a value of 5;
Het is a six-membered saturated heterocycle containing five carbon atoms and one nitrogen atom, wherein Het is attached to the —$(CH_2)_n$— moiety at the carbon 4 position of the heterocycle; and
$R^3$ is hydrogen;
or a pharmaceutically acceptable salt thereof.

In a further aspect of the invention, $R^1$ is selected from 1-methylbutoxy and (1S)-1-methylbutoxy.

In a further aspect of the invention, $R^1$ is 1-methylbutoxy.

In a further aspect of the invention, $R^1$ is (1S)-1-methylbutoxy.

A further aspect of the invention is a compound of formula (I), wherein
$R^1$ is (1S)-1-methylbutoxy;
$R^2$ is a group having the structure:

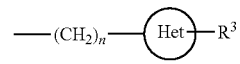

where n is an integer having a value of 5;
Het is piperidine, where Het is attached to the —$(CH_2)_n$— moiety at the carbon 4 position of the heterocycle; and
$R^3$ is hydrogen;
or a pharmaceutically acceptable salt thereof.

A further aspect of the invention is the compound 6-amino-9-[5-(4-piperidinyl)pentyl]2-[(1S)- 1-methylbutyl]oxy]-7,9-dihydro-8H-purin-8-one or a pharmaceutically acceptable salt thereof.

There is provided as a further aspect of the invention a compound of formula (I), or a pharmaceutically acceptable salt thereof, for use in therapy. It will be appreciated that, when a compound of formula (I) or a pharmaceutically acceptable salt thereof is used in therapy, it is used as an active therapeutic agent.

There is provided as a further aspect of the invention the compound 6-amino-9-[5-(4-piperidinyl)pentyl]-2-[(1S)-1-methylbutyl]oxy]-7,9-dihydro-8H-purin-8-one, or a pharmaceutically acceptable salt thereof, for use in therapy. It will be appreciated that, when the compound 6-amino-9-[5-(4-piperidinyl)pentyl]-2-[(1S)-1-methylbutyl]oxy]-7,9-dihydro-8H-purin-8-one, or a pharmaceutically acceptable salt thereof, is used in therapy, it is used as an active therapeutic agent.

There is also therefore provided a compound of formula (I), or a pharmaceutically acceptable salt thereof, for use in the treatment of allergic diseases or other inflammatory conditions, infectious diseases, or cancer.

There is also therefore provided the compound 6-amino-9-[5-(4-piperidinyl)pentyl]-2-[(1S)-1-methylbutyl]oxy]-7,9-dihydro-8H-purin-8-one or a pharmaceutically acceptable salt thereof, for use in the treatment of allergic diseases or other inflammatory conditions, infectious diseases, or cancer.

There is also therefore provided a compound of formula (I), or a pharmaceutically acceptable salt thereof, for use in the treatment of allergic rhinitis.

There is also provided the compound 6-amino-9-[5-(4-piperidinyl)pentyl]-2-[(1S)-1-methylbutyl]oxy]-7,9-dihydro-8H-purin-8-one or a pharmaceutically acceptable salt thereof, for use in the treatment of allergic rhinitis.

There is also therefore provided a compound of formula (I), or a pharmaceutically acceptable salt thereof, for use in the treatment of asthma.

There is also therefore provided the compound 6-amino-9-[5-(4-piperidinyl)pentyl]-2-[(1S)-1-methylbutyl]oxy]-7,9-dihydro-8H-purin-8-one, or a pharmaceutically acceptable salt thereof, for use in the treatment of asthma.

There is further provided an immunogenic composition comprising an antigen or antigen composition and a compound of formula (I), or a pharmaceutically acceptable salt thereof.

There is further provided an immunogenic composition comprising an antigen or antigen composition and the compound 6-amino-9-[5-(4-piperidinyl)pentyl]-2-[(1S)-1-methylbutyl]oxy]-7,9-dihydro-8H-purin-8-one, or a pharmaceutically acceptable salt thereof.

There is further provided a vaccine composition comprising an antigen or antigen composition and a compound of formula (I), or a pharmaceutically acceptable salt thereof.

There is further provided a vaccine composition comprising an antigen or antigen composition and the compound 6-amino-9-[5-(4-piperidinyl)pentyl]-2-[(1S)-1-methylbutyl]oxy]-7,9-dihydro-8H-purin-8-one, or a pharmaceutically acceptable salt thereof.

There is further provided a method of treating or preventing disease comprising the administration to a human subject suffering from or susceptible to disease, an immunogenic composition comprising an antigen or antigen composition and a compound of formula (I), or a pharmaceutically acceptable salt thereof.

There is further provided a method of treating or preventing disease comprising the administration to a human subject suffering from or susceptible to disease, an immunogenic composition comprising an antigen or antigen composition and the compound 6-amino-9-[5-(4-piperidinyl)pentyl]-2-[(1S)-1-methylbutyl]oxy]-7,9-dihydro-8H-purin-8-one, or a pharmaceutically acceptable salt thereof.

There is further provided a method of treating or preventing disease comprising the administration to a patient human subject suffering from or susceptible to disease, a vaccine composition comprising an antigen or antigen composition and a compound of formula (I), or a pharmaceutically acceptable salt thereof.

There is further provided a method of treating or preventing disease comprising the administration to a patient human subject suffering from or susceptible to disease, a vaccine composition comprising an antigen or antigen composition and the compound 6-amino-9-[5-(4-piperidinyl)pentyl]-2-[(1S)-1-methylbutyl]oxy]-7,9-dihydro-8H-purin-8-one, or a pharmaceutically acceptable salt thereof.

There is further provided the use of a compound of formula (I), or a pharmaceutically acceptable salt thereof, for the manufacture of an immunogenic composition comprising an antigen or antigen composition, for the treatment or prevention of disease.

There is further provided the use of the compound 6-amino-9-[5-(4-piperidinyl)pentyl]-2-[(1S)-1-methylbutyl]oxy]-7,9-dihydro-8H-purin-8-one, or a pharmaceutically acceptable salt thereof, for the manufacture of an immunogenic composition comprising an antigen or antigen composition, for the treatment or prevention of disease.

There is further provided the use of a compound of formula (I), or a pharmaceutically acceptable salt thereof, for the manufacture of a vaccine composition comprising an antigen or antigen composition, for the treatment or prevention of disease.

There is further provided the use of the compound 6-amino-9-[5-(4-piperidinyl)pentyl]-2-[(1S)-1-methylbutyl]oxy]-7,9-dihydro-8H-purin-8-one, or a pharmaceutically acceptable salt thereof, for the manufacture of a vaccine composition comprising an antigen or antigen composition, for the treatment or prevention of disease.

There is further provided the use of a compound of formula (I), or a pharmaceutically acceptable salt thereof, for the manufacture of a medicament for the treatment of allergic diseases or other inflammatory conditions, infectious diseases, or cancer.

There is further provided the use of the compound 6-amino-9-[5-(4-piperidinyl)pentyl]-2-[(1S)-1-methylbutyl]oxy]-7,9-dihydro-8H-purin-8-one, or a pharmaceutically acceptable salt thereof, for the manufacture of a medicament for the treatment of allergic diseases or other inflammatory conditions, infectious diseases, or cancer.

There is further provided the use of a compound of formula (I), or a pharmaceutically acceptable salt thereof, for the manufacture of a medicament for the treatment of allergic rhinitis.

There is further provided the use of the compound 6-amino-9-[5-(4-piperidinyl)pentyl]-2-[(1S)-1-methylbutyl]oxy]-7,9-dihydro-8H-purin-8-one, or a pharmaceutically acceptable salt thereof, for the manufacture of a medicament for the treatment of allergic rhinitis.

There is further provided the use of a compound of formula (I), or a pharmaceutically acceptable salt thereof, for the manufacture of a medicament for the treatment of asthma.

There is further provided the use of the compound 6-amino-9-[5-(4-piperidinyl)pentyl]-2-[(1S)-1-methylbutyl]oxy]-7,9-dihydro-8H-purin-8-one, or a pharmaceutically acceptable salt thereof, for the manufacture of a medicament for the treatment of asthma.

There is further provided a method of treatment of allergic diseases or other inflammatory conditions, infectious diseases, or cancer, which method comprises administering to a human subject in need thereof a therapeutically effective amount of a compound of formula (I), or a pharmaceutically acceptable salt thereof.

There is further provided a method of treatment of allergic diseases or other inflammatory conditions, infectious diseases, or cancer, which method comprises administering to a human subject in need thereof a therapeutically effective amount of the compound 6-amino-9-[5-(4-piperidinyl)pentyl]-2-[(1S)-1-methylbutyl]oxy]-7,9-dihydro-8H-purin-8-one, or a pharmaceutically acceptable salt thereof.

There is further provided a method of treatment of allergic rhinitis, which method comprises administering to a human subject in need thereof a therapeutically-effective amount of a compound of formula (I), or a pharmaceutically acceptable salt thereof.

There is further provided a method of treatment of allergic rhinitis, which method comprises administering to a human subject in need thereof a therapeutically-effective amount of the compound 6-amino-9-[5-(4-piperidinyl)pentyl]-2-[(1S)-1-methylbutyl]oxy]-7,9-dihydro-8H-purin-8-one, or a pharmaceutically acceptable salt thereof.

There is further provided a method of treatment of asthma, which method comprises administering to a human subject in need thereof a therapeutically effective amount of a compound of formula (I), or a pharmaceutically acceptable salt thereof.

There is further provided a method of treatment of asthma, which method comprises administering to a human subject in need thereof a therapeutically effective amount of the compound 6-amino-9-[5-(4-piperidinyl)pentyl]-2-[(1S)-1-methylbutyl]oxy]-7,9-dihydro-8H-purin-8-one, or a pharmaceutically acceptable salt thereof.

The invention provides in a further aspect, a combination comprising a compound of formula (I), or a pharmaceutically acceptable salt thereof, together with at least one other therapeutically active agent.

The invention provides in a further aspect, a combination comprising the compound 6-amino-9-[5-(4-piperidinyl)pentyl]-2-[(1S)-1-methylbutyl]oxy]-7,9-dihydro-8H-purin-8-one, or a pharmaceutically acceptable salt thereof, together with at least one other therapeutically active agent.

There is further provided a pharmaceutical composition comprising a compound of formula (I), or a pharmaceutically acceptable salt thereof, and one or more pharmaceutically acceptable diluents or carriers.

There is further provided a pharmaceutical composition comprising the compound 6-amino-9-[5-(4-piperidinyl)pentyl]-2-[(1S)-1-methylbutyl]oxy]-7,9-dihydro-8H-purin-8-one, or a pharmaceutically acceptable salt thereof, and one or more pharmaceutically acceptable diluents or carriers.

There is also provided a process for preparing a pharmaceutical composition which comprises admixing a compound of formula (I), or a pharmaceutically acceptable salt thereof, with one or more pharmaceutically acceptable diluents or carriers.

There is also provided a process for preparing a pharmaceutical composition which comprises admixing the compound 6-amino-9-[5-(4-piperidinyl)pentyl]-2-[(1S)-1-methylbutyl]oxy]-7,9-dihydro-8H-purin-8-one, or a pharmaceutically acceptable salt thereof, with one or more pharmaceutically acceptable diluents or carriers.

The compounds of the invention and salts thereof may be prepared by the methodology described herein, which constitutes a further aspect of this invention.

Accordingly, there is provided a process for the preparation of a compound of formula (I), or the compound 6-amino-9-[5-(4-piperidinyl)pentyl]-2-[(1S)-1-methylbutyl]oxy]-7,9-dihydro-8H-purin-8-one, which process comprises the deprotection of a compound of formula (II):

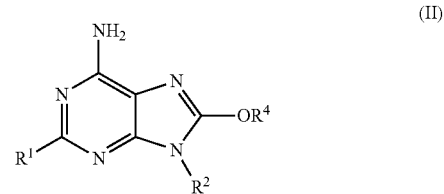

(II)

wherein $R^1$ and $R^2$ are as hereinbefore defined for a compound of formula (I) and $R^4$ is $C_{1-6}$alkyl, and thereafter, if required, carrying out one or more of the following optional steps:

(i) removing any necessary protecting group;
(ii) preparing a salt of the compound so-formed.

There is further provided a process for the preparation of a compound of formula (I), or the compound 6-amino-9-[5-(4-piperidinyl)pentyl]-2-[(1S)-1-methylbutyl]oxy]-7,9-dihydro-8H-purin-8-one, which process comprises converting a compound of formula (II) to a further compound of formula (IIP) and thereafter, if required, carrying out one or more of the following optional steps:

(i) removing any necessary protecting group;
(ii) preparing a salt of the compound so-formed.

In a further embodiment, a compound of formula (I), or the compound 6-amino-9-[5-(4-piperidinyl)pentyl]-2-[(1S)-1-methylbutyl]oxy]-7,9-dihydro-8H-purin-8-one, may also be prepared by deprotection of a compound of formula (IIP):

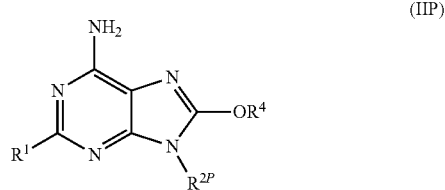

(IIP)

wherein $R^1$ is as hereinbefore defined for a compound of formula (I), $R^4$ is as hereinbefore defined for a compound of formula (II), and $R^{2P}$ is a protected $R^2$ group wherein the protecting group is a suitable protecting group, for example a tert-butoxycarbonyl (Boc) group or a carbobenzyloxy group, and thereafter, if required, carrying out one or more of the following optional steps:

(i) removing any necessary protecting group;
(ii) preparing a salt of the compound so-formed.

The present invention covers all combinations of embodiments and aspects herein described.

DETAILED DESCRIPTION OF THE INVENTION

Figure 1A:
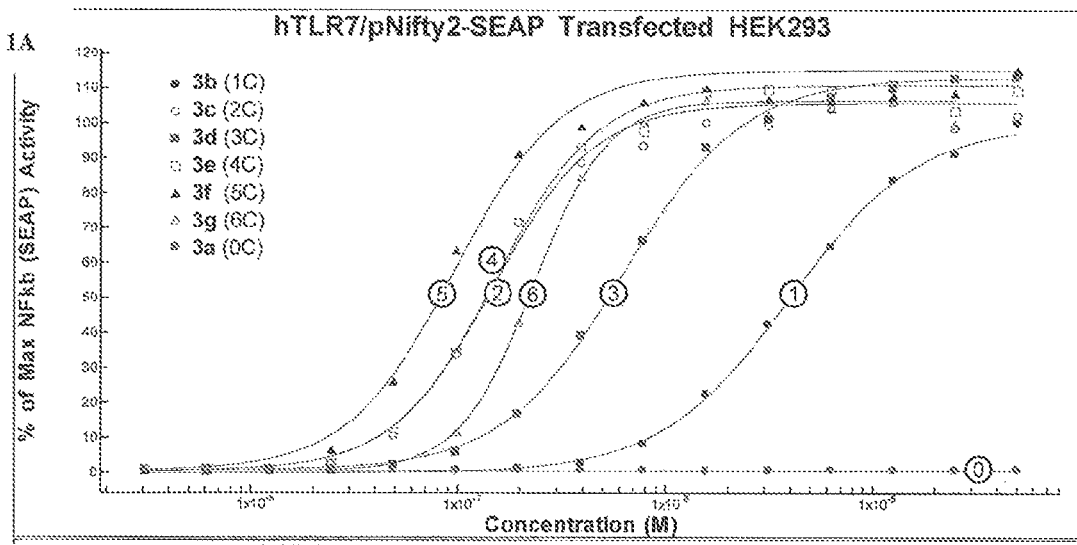
FIG. 1 graphs NFKB response of (A) HEK293-hTLR7 and (B) HEK293-hTLR8 cells treated for 24 hours with oxoadenine compounds 3a-3g; (C) shows hTLR7and hTLR8 $EC_{50}$ values for oxoadenines 3a-3g. Circled numbers on the graph indicate the carbon linker length of each compound.

Described herein is the synthesis of oxoadenine compounds substituted at the C9 position with a piperidinylalkyl moiety, and containing a C2 butoxy or methylbutoxy. In vitro evaluation in HEK293 cells transfected with human TLR7 or human TLR8, and in human PBMCs, indicated that hTLR7/8 selectivity/potency and cytokine induction could be modulated by varying the length of the carbon linker. Additionally, it was determined that introduction of a methyl group on the first carbon of the C2-butoxy (to provide methylbutoxy) affected both TLR7 and TLR8 activity.

Oligonucleotide agonists of TLR7 and TLR9, and small molecule purine-based agonists of TLR7, have been described which can induce interferon alpha from these cell types in animals and in man (Takeda K. et al, *Annu. Rev. Immunol.*, 2003: 21, 335-76). TLR7 agonists include imidazoquinoline compounds such as imiquimod and resiquimod, oxoadenine analogues and also nucleoside analogues such as loxoribine and 7-thia-8-oxoguanosine, which are known to induce interferon alpha.

International Patent Application publication number WO 2007/034882 (PCT/JP2006/318758; Dainippon Sumitomo Pharma Co. Ltd./AstraZeneca Aktiebolag) discloses certain adenine compounds identified as useful as medicine.

Certain adenine derivative compounds described in WO 2010/018134 (PCT/EP2009/060267) have been shown to be inducers of human interferon and may possess an improved profile (with respect to certain other known inducers of human interferon), for example enhanced potency, and may show enhanced selectivity for IFNα with respect to Tumor Necrosis Factor alpha (TNFα). For example, certain compounds indicate greater than 1000-fold selectivity for IFNα induction over TNFα induction. Compounds which induce human interferon may be useful as vaccine adjuvants. Compounds which induce human interferon may be useful in the treatment of various disorders, including infectious diseases, cancer, inflammatory conditions, and allergic diseases. Compounds which induce human interferon may be useful in the treatment of allergic rhinitis or asthma.

The present invention is described in terms known and appreciated by those skilled in the art. For ease of reference certain terms hereinafter are defined. The fact that certain terms are defined, however, should not be considered as indicative that defined terms are used in a manner inconsistent with the ordinary meaning or, alternatively, that any term that is undefined is indefinite or not used within the ordinary and accepted meaning. Rather, all terms used herein are believed to describe the invention such that one of ordinary skill can appreciate the scope of the present invention. The following definitions are meant to clarify, but not limit, the terms defined.

References to 'alkyl' includes reference to both straight-chain and branched-chain aliphatic isomers of the corresponding alkyl containing up to eight carbon atoms, for example up to six carbon atoms, or up to four carbon atoms, or up to two carbon atoms, or one carbon atom. Such references to 'alkyl' are also applicable when an alkyl group is part of another group, for example an alkylamino or alkoxy group. Examples of such alkyl groups and groups containing alkyl groups are $C_{1-8}$ alkyl, $C_{1-6}$ alkyl, $C_{1-6}$ alkylamino, and $C_{1-6}$ alkoxy.

References to 'heterocycle' or 'heterocyclyl' refer to a monocyclic saturated heterocyclic aliphatic ring containing five carbon atoms and at least one heteroatom, which heteroatom is nitrogen, oxygen or sulfur. Such heterocyclic rings include piperidine or piperidinyl, where the ring contains five carbon atoms and a nitrogen heteroatom.

As used herein with regard to compounds of Formula I, 'carbon linker' refers to the —$(CH_2)_n$— moiety, and may alternately be referred to as 'alkyl linker'. Thus a "five-carbon" linker is —$(CH_2)_5$—.

Throughout this specification the generally accepted atom numbering system of the purine skeleton is used:

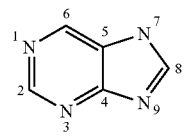

The following list provides definitions of certain abbreviations as used herein. The list is not exhaustive; the meaning of abbreviations not defined below will be readily apparent to those of ordinary skill in the art.

DCM dichloromethane
DMF N,N-dimethylformamide
DMSO dimethyl sulfoxide
ELISA enzyme linked immunosorbent assay
EtOAc ethyl acetate
H hours
HCl hydrochloric acid
$Et_3N$ triethylamine
L litres LCMS liquid chromatography—mass spectrometry
Mins minutes
MS mass spectrometry
NFkB nuclear factor kappa B
NMR nuclear magnetic resonance
ssNMR solid state nuclear magnetic resonance
PBMC peripheral blood mononuclear cells
PBS phosphate buffered saline
PRR pattern-recognition receptor
RT room temperature
Stripped removal of solvent under reduced pressure
TFA trifluoroacetic acid
TLR toll-like receptor
RT room temperature It is to be understood that references herein to compounds of the invention mean a compound of formula (I) as the free base, or as a salt, for example a pharmaceutically acceptable salt.

Salts of the compounds of formula (I) include pharmaceutically acceptable salts and salts which may not be pharmaceutically acceptable but which may be useful in the preparation of compounds of formula (I) and pharmaceutically acceptable salts thereof. Salts may be derived from certain inorganic or organic acids, or certain inorganic or organic bases.

The invention includes within its scope all possible stoichiometric and non-stoichiometric forms of the salts of the compounds of formula (I).

Examples of salts are pharmaceutically acceptable salts. Pharmaceutically acceptable salts include acid addition salts and base addition salts. For a review on suitable salts see, e.g., Berge et al., *J. Pharm. Sci.*, 66:1-19 (1977).

Examples of pharmaceutically acceptable acid addition salts of a compound of formula (I) include hydrobromide, hydrochloride, sulphate, p-toluenesulphonate, methanesulphonate, naphthalenesulphonate, and phenylsulphonate salts.

Examples of pharmaceutically acceptable base salts include alkali metal salts such as those of sodium and potassium, and alkaline earth metal salts such as those of calcium and magnesium.

Salts may be formed using techniques well-known in the art, for example by precipitation from solution followed by filtration, or by evaporation of the solvent.

Typically, a pharmaceutically acceptable acid addition salt can be formed by reaction of a compound of formula (I) with a suitable strong acid (such as hydrobromic, hydrochloric, sulphuric, p-toluenesulphonic, methanesulphonic or naphthalenesulphonic acids), optionally in a suitable solvent such as an organic solvent, to give the salt which is usually isolated for example by crystallisation and filtration.

It will be appreciated that many organic compounds can form complexes with solvents in which they are reacted or from which they are precipitated or crystallised.

These complexes are known as "solvates". For example, a complex with water is known as a "hydrate". Solvents with high boiling points and/or solvents with a high propensity to form hydrogen bonds such as water, ethanol, iso-propyl alcohol, and N-methyl pyrrolidinone may be used to form solvates. Methods for the identification of solvates include, but are not limited to, NMR and microanalysis The compounds and salts of the invention may exist in solvated and unsolvated forms As used herein, the term solvate encompasses solvates of both a free base compound as well as any salt thereof.

Certain of the compounds of the invention may contain chiral atoms and/or multiple bonds, and hence may exist in one or more stereoisomeric forms. The present invention encompasses all of the stereoisomers of the compounds of the invention, including optical isomers, whether as individual stereoisomers or as mixtures thereof including racemic modifications. Any stereoisomer may contain less than 10% by weight, for example less than 5% by weight, or less than 0.5% by weight, of any other stereoisomer. For example, any optical isomer may contain less than 10% by weight, for example less than 5% by weight, or less than 0.5% by weight, of its antipode.

Certain of the compounds of the invention may exist in tautomeric forms. It will be understood that the present invention encompasses all of the tautomers of the compounds of the invention whether as individual tautomers or as mixtures thereof whether or not explicitly indicated in the present formulas.

The compounds of the invention may be in crystalline or amorphous form. Furthermore, some of the crystalline forms of the compounds of the invention may exist as polymorphs, all of which are included within the scope of the present invention. The most thermodynamically stable polymorphic form or forms of the compounds of the invention are of particular interest.

Polymorphic forms of compounds of the invention may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

It will be appreciated from the foregoing that included within the scope of the invention are hydrates, isomers and polymorphic forms of the compounds of formula (I) and salts thereof.

Examples of disease states in which the compounds of formula (I) and pharmaceutically acceptable salts thereof have potentially beneficial effects include allergic diseases and other inflammatory conditions (for example allergic rhinitis and asthma), infectious diseases, and cancer. The compounds of formula (I) and pharmaceutically acceptable salts thereof are also of potential use as vaccine adjuvants.

As modulators of the immune response the compounds of formula (I) and pharmaceutically acceptable salts thereof may also be useful as a therapeutic, either alone or in combination with other compounds, in the treatment and/or prevention of immune-mediated disorders, including but not limited to inflammatory or allergic diseases such as asthma, allergic rhinitis and rhinoconjuctivitis, food allergy, hypersensitivity lung diseases, eosinophilic pneumonitis, delayed-type hypersensitivity disorders, atherosclerosis, pancreatitis, gastritis, colitis, osteoarthritis, psoriasis, sarcoidosis, pulmonary fibrosis, respiratory distress syndrome, bronchiolitis, chronic obstructive pulmonary disease, sinusitis, cystic fibrosis, actinic keratosis, skin dysplasia, chronic urticaria, eczema and all types of dermatitis.

As used herein, prevention (or prophylaxis) of disease refers to the administration or use of a compound or composition in a subject, before the subject has developed a particular disease, in order to reduce the chance of the subject developing the disease or to reduce the severity of the disease should the subject develope it. Thus, while prevention or prophylaxis may not prevent development of disease in every subject treated, the occurrence or severity of the disease in a group of treated subjects will be improved compared to a control group of untreated subjects.

The compounds of formula (I) and pharmaceutically acceptable salts thereof may also be useful in the treatment and/or prevention of reactions against respiratory infections, including but not limited to airways viral exacerbations and tonsillitis. The compounds may also be useful in the treatment and/or prevention of autoimmune diseases including but not limited to rheumatoid arthritis, psoriatic arthritis, systemic lupus erythematosus, Sjöegrens disease, ankylosing spondylitis, scleroderma, dermatomyositis, diabetes, graft rejection, including graft-versus-host disease, inflammatory bowel diseases including, but not limited to, Crohn's disease and ulcerative colitis.

The compounds of formula (I) and pharmaceutically acceptable salts thereof may also be useful in the treatment of infectious diseases including, but not limited to, those caused by hepatitis viruses (e.g. hepatitis B virus, hepatitis C virus), human immunodeficiency virus, papillomaviruses, herpesviruses, respiratory viruses (e.g. influenza viruses, respiratory syncytial virus, rhinovirus, metapneumovirus, parainfluenzavirus, SARS), and West Nile virus. The compounds of formula (I) and pharmaceutically acceptable salts thereof may also be useful in the treatment of microbial infections caused by, for example, bacteria, fungi, or protozoa. These include, but are not limited to, tuberculosis, bacterial pneumonia, aspergillosis, histoplasmosis, candidosis, pneumocystosis, leprosy, chlamydia, cryptococcal disease, cryptosporidosis, toxoplasmosis, leishmania, malaria, and trypanosomiasis.

The compounds of formula (I) and pharmaceutically acceptable salts thereof may also be useful in the treatment of various cancers, in particular the treatment of cancers that are known to be responsive to immunotherapy and including, but not limited to, renal cell carcinoma, lung cancer, breast cancer, colorectal cancer, bladder cancer, melanoma, leukaemia, lymphomas and ovarian cancer.

A 'subject', as used herein, comprises mammalian subjects, and includes non-primate mammalian subjects, primate subjects, and human subjects. As used herein, therapy or treatment of a disease refers to an action capable of ameliorating symptoms of the disease, and/or extending the expected life-expectancy or disease-free survival of a subject suffering from the disease. References herein to treatment or therapy may, depending on the condition, extend to prophylactic treatment to reduce the risk that a subject will contract or develop a disease.

As mentioned herein, compounds of formula (I) and pharmaceutically acceptable salts thereof may be useful as therapeutic agents.

The compounds of formula (I) and pharmaceutically acceptable salts thereof may be formulated for administration in any convenient way.

The compounds of formula (I) and pharmaceutically acceptable salts thereof may, for example, be formulated for oral, topical, inhaled, intranasal, buccal, parenteral (for example intravenous, subcutaneous, intradermal, or intramuscular) or rectal administration. In one aspect, the compounds of formula (I) and pharmaceutically acceptable salts thereof are formulated for oral administration. In a further aspect, the compounds of formula (I) and pharmaceutically acceptable salts thereof are formulated for topical administration, for example intranasal or inhaled administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Compositions for intranasal administration include aqueous compositions administered to the nose by drops or by pressurised pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulisation.

Intranasal compositions may permit the compound(s) of formula (I) or pharmaceutically acceptable salt(s) thereof to be delivered to all areas of the nasal cavities (the target tissue) and further, may permit the compound(s) of formula (I) or pharmaceutically acceptable salt(s) thereof to remain in contact with the target tissue for longer periods of time. A suitable dosing regime for intranasal compositions would be for the patient to inhale slowly through the nose subsequent to the nasal cavity being cleared. During inhalation the composition would be administered to one nostril while the other is manually compressed. This procedure would then be repeated for the other nostril. Typically, one or two sprays per nostril would be administered by the above procedure one, two, or three times each day, ideally once daily. Of particular interest are intranasal compositions suitable for once-daily administration.

The suspending agent(s), if included, will typically be present in an amount of from 0.1 to 5% (w/w), such as from 1.5% to 2.4% (w/w), based on the total weight of the composition. Examples of pharmaceutically acceptable suspending agents include, but are not limited to, AVICEL® (microcrystalline cellulose and carboxymethylcellulose sodium), carboxymethylcellulose sodium, veegum, tragacanth, bentonite, methylcellulose, xanthan gum, carbopol and polyethylene glycols.

Compositions for administration to the lung or nose may contain one or more excipients, and may be protected from microbial or fungal contamination and growth by inclusion of one or more preservatives. Examples of pharmaceutically acceptable anti-microbial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives include, but are not limited to, sodium benzoate, sorbic acid, sodium propionate, methylparaben, ethylparaben, propylparaben and butylparaben. The preservative(s), if included, may be present in an amount of from 0.001 to 1% (w/w), such as from 0.015% to 0.5% (w/w) based on the total weight of the composition.

Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing. Examples of pharmaceutically acceptable surfactants include fatty alcohols, esters and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids e.g. fluids of the nasal cavity, resulting in reduced levels of irritancy. Examples of pharmaceutically acceptable tonicity adjusting agents include, but are not limited to, sodium chloride, dextrose, xylitol, calcium chloride, glucose, glycerine and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the invention may be buffered by the addition of suitable buffering agents such as sodium citrate, citric acid, trometamol, phosphates such as disodium phosphate (for example the dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, eucalyptus oil, camphor, a natural flavouring agent, an artificial flavouring agent, and combinations thereof.

One or more co-solvent(s) may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol. In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueous/organic mixtures, dry powder or crystalline compositions administered to the respiratory tract by pressurised pump or inhaler, for example, reservoir dry powder inhalers, unit-dose dry powder inhalers, pre-metered multi-dose dry powder inhalers, nasal inhalers or pressurised aerosol inhalers, nebulisers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulisation. Such compositions may be aqueous solutions or suspensions or aerosols delivered from pressurised packs, such as a metered dose inhaler, with the use of a suitable liquefied propellant.

Compositions for administration topically to the nose (for example, for the treatment of rhinitis) or to the lung, include pressurised aerosol compositions and aqueous compositions delivered to the nasal cavities by pressurised pump. Compositions which are non-pressurised and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity. A fluid dispenser of the aforementioned type is described and illustrated in International Patent Application publication number WO 2005/044354 (Glaxo Group Limited). In one embodiment, the fluid dispenser is of the general type illustrated in FIGS. 30-40 of WO 2005/044354.

Aqueous compositions containing a compound of formula (I) or a pharmaceutically acceptable salt thereof may also be delivered by a pump as disclosed in International Patent Application publication number WO2007/138084 (Glaxo Group Limited), for example as disclosed with reference to FIGS. 22-46 thereof, or as disclosed in WO2011/098451 (Glaxo Group Limited, GB0723418.0), for example as disclosed with reference to FIGS. 7-32 thereof. The pump may be actuated by an actuator as disclosed in FIGS. 1-6 of WO2011/098451.

Dry powder compositions for topical delivery to the lung by inhalation may, for example, be presented in capsules and cartridges of for example gelatine, or blisters of for example laminated aluminium foil, for use in an inhaler or insufflator. Powder blend compositions generally contain a powder mix for inhalation of the compound of formula (I) or a pharmaceutically acceptable salt thereof and a suitable powder base (carrier/diluent/excipient substance) such as mono-, di-, or polysaccharides (for example lactose or starch). Dry powder compositions may also include, in addition to the drug and carrier, a further excipient (for example a ternary agent such as a sugar ester for example cellobiose octaacetate, calcium stearate, or magnesium stearate.

In one embodiment, a composition suitable for inhaled administration may be incorporated into a plurality of sealed dose containers provided on medicament pack(s) mounted inside a suitable inhalation device. The containers may be rupturable, peelable, or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ and DISKUS™ devices, marketed by GlaxoSmithKline.

A dry powder inhalable composition may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ (AstraZeneca), TWISTHALER™ (Schering) and CLICKHALER™ (Innovata.)

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ (GlaxoSmithKline) and HANDIHALER™ (Boehringer Ingelheim.)

Pressurised aerosol compositions suitable for inhalation can be either a suspension or a solution and may contain a compound of formula (I) or a pharmaceutically acceptable salt thereof and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional composition excipients well known in the art such as surfactants e.g. oleic acid, lecithin or an oligolactic acid or derivative thereof e.g. as described in WO 94/21229 and WO 98/34596 (Minnesota Mining and Manufacturing Company) and co-solvents e.g. ethanol. Pressurised compositions will generally be retained in a canister (e.g. an aluminium canister) closed with a valve (e.g. a metering valve) and fitted into an actuator provided with a mouthpiece.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, wool-fat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

The compounds of formula (I) and pharmaceutically acceptable salts thereof may, for example, be formulated for transdermal delivery by composition into patches or other devices (e.g. pressurised gas devices) which deliver the active component into the skin.

For buccal administration the compositions may take the form of tablets or lozenges formulated in the conventional manner.

The compounds of formula (I) and pharmaceutically acceptable salts thereof may also be formulated as suppositories, e.g. containing conventional suppository bases such as cocoa butter or other glycerides.

The compounds of formula (I) and pharmaceutically acceptable salts thereof may also be formulated for parenteral administration by bolus injection or continuous infusion and may be presented in unit dose form, for instance as ampoules, vials, small volume infusions or pre-filled syringes, or in multidose containers with an added preservative. The compositions may take such forms as solutions, suspensions, or emulsions in aqueous or non-aqueous vehicles, and may contain formulatory agents such as antioxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The compounds of formula (I) and pharmaceutically acceptable salts thereof may also be formulated with vaccines as adjuvants. Such compositions may contain antibody(ies) or antibody fragment(s) or an antigenic component including but not limited to protein, DNA, live or dead bacteria and/or viruses or virus-like particles, together with one or more components with adjuvant activity including but not limited to aluminium salts, oil and water emulsions, heat shock proteins, lipid A preparations and derivatives, glycolipids, other TLR agonists such as CpG DNA or similar agents, cytokines such as Granulocyte Macrophage Colony-Stimulating Factor (GM-CSF) or Interleukin-12 (IL-12) or similar agents.

The compounds of formula (I) and pharmaceutically acceptable salts thereof may be employed alone or in combination with other therapeutic agents. The compounds of formula (I) and pharmaceutically acceptable salts thereof and the other pharmaceutically active agent(s) may be administered together or separately and, when administered separately, administration may occur simultaneously or sequentially, in any order. The amounts of the compound(s) of formula (I) or pharmaceutically acceptable salt(s) thereof and the other pharmaceutically active agent(s) and the relative timings of administration will be selected in order to achieve the desired combined therapeutic effect. The administration of a combination of a compound of formula (I) or a pharmaceutically acceptable salt thereof with other treatment agents may be in combination by administration concomitantly in a unitary pharmaceutical composition including both compounds, or in separate pharmaceutical compositions each including one of the compounds. Alternatively, the combination may be administered separately in a sequential manner wherein one treatment agent is administered first and the other second or vice versa. Such sequential administration may be close in time or remote in time.

The compounds of formula (I) and pharmaceutically acceptable salts thereof may be used in combination with one or more agents useful in the prevention or treatment of viral infections. Examples of such agents include, without limitation; polymerase inhibitors such as those disclosed in WO 2004/037818-A1, as well as those disclosed in WO 2004/037818 and WO 2006/045613; JTK-003, JTK-019, NM-283, HCV-796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents; replication inhibitors such as acyclovir, famciclovir, ganciclovir, cidofovir, lamivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; and similar agents; nucleoside and nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, elvucitabine, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC-125, etravirine, and similar agents; entry inhibitors such as enfuvirtide (T-20), T-1249, PRO-542, PRO-140, TNX-355, BMS-806, 5-Helix and similar agents; integrase inhibitors such as L-870,180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 02/74769, WO 2004/054974, WO 2004/055012, WO 2004/055010, WO 2004/055016, WO 2004/055011, and WO 2004/054581, and similar agents; neuraminidase inhibitors such as CS-8958, zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/105761, WO 2003/085375, WO 2006/122011, ribavirin, and similar agents. The compounds of formula (I) and pharmaceutically acceptable salts thereof may also be used in combination with one or more other agents which may be useful in the prevention or treatment of viral infections for example immune therapies (e.g. interferon or other cytokines/chemokines, cytokine/chemokine receptor modulators, cytokine agonists or antagonists and similar agents); and therapeutic vaccines, antifibrotic agents, anti-inflammatory agents such as corticosteroids or non-steroidal anti-inflammatory agents (NSAIDs) and similar agents.

The compounds of formula (I) and pharmaceutically acceptable salts thereof may be used in combination with one or more other agents which may be useful in the prevention or treatment of allergic disease, inflammatory disease, autoimmune disease, for example: antigen immunotherapy, anti-histamines, steroids, non-steroidal anti-inflammatories (NSAIDs), bronchodilators (e.g. beta 2 agonists, adrenergic agonists, anticholinergic agents, theophylline), methotrexate, leukotriene modulators and similar agents; monoclonal antibody therapy such as anti-Immunoglobulin E (IgE), anti-TNF, anti-IL-5, anti-IL-6, anti-IL-12, anti-IL-1 and similar agents; receptor therapies e.g. entanercept and similar agents; antigen non-specific immunotherapies (e.g. interferon or other cytokines/chemokines, cytokine/chemokine receptor modulators, cytokine agonists or antagonists, TLR agonists and similar agents).

The compounds of formula (I) and pharmaceutically acceptable salts thereof may be used in combination with one or more other agents which may be useful in the prevention or treatment of cancer, for example chemotherapeutics such as alkylating agents, topoisomerase inhibitors, antimetabolites, antimitotic agents, kinase inhibitors and similar agents; monoclonal antibody therapy such as trastuzumab, gemtuzumab and other similar agents; and hormone therapy such as tamoxifen, goserelin and similar agents.

The pharmaceutical compositions according to the invention may also be used alone or in combination with at least one other therapeutic agent in other therapeutic areas, for example gastrointestinal disease. The compositions according to the invention may also be used in combination with gene replacement therapy.

The invention includes in a further aspect a combination comprising a compound of formula (I), or a pharmaceutically acceptable salt thereof, together with at least one other therapeutically active agent.

The combinations referred to above may conveniently be presented for use in the form of a pharmaceutical composition and thus pharmaceutical compositions comprising a combination as defined above together with at least one pharmaceutically acceptable diluent or carrier thereof represent a further aspect of the invention.

A therapeutically effective amount of a compound of formula (I) or a pharmaceutically acceptable salt thereof will depend upon a number of factors. For example, the species, age, and weight of the recipient subject, the precise condition requiring treatment and its severity, the nature of the composition, and the route of administration are all factors to be considered. The therapeutically effective amount ultimately should be at the discretion of the attendant physician. Regardless, an effective amount of a compound of the present invention for the treatment of humans generally should be in the range of 0.0001 to 100 mg/kg body weight of recipient per day. More usually the effective amount should be in the range of 0.001 to 10 mg/kg body weight per day. Thus, for a 70 kg adult one example of an actual amount per day would usually be from 7 to 700 mg. For intranasal and inhaled routes of administration, typical doses for a 70 kg adult should be in the range of 1 microgramme to 1 mg per day. This amount may be given in a single dose per day or in a number (such as two, three, four, five, or more) of sub-doses per day such that the total daily dose is the same. An effective amount of a pharmaceutically acceptable salt of a compound of formula (I) may be determined as a proportion of the effective amount of the compound of formula (I) or a pharmaceutically acceptable salt thereof per se. Similar dosages should be appropriate for treatment of the other conditions referred to herein.

Compounds of formula (I) and pharmaceutically acceptable salts thereof may also be administered at any appropriate frequency e.g. 1-7 times per week. The precise dosing regimen will of course depend on factors such as the therapeutic indication, the age and condition of the subject, and the particular route of administration chosen.

Pharmaceutical compositions may be presented in unit-dose forms containing a predetermined amount of active ingredient per unit dose. Such a unit may contain, as a non-limiting example, 0.5 mg to 1 g of a compound of formula (I) or a pharmaceutically acceptable salt thereof, depending on the condition being treated, the route of administration, and the age, weight, and condition of the patient. Preferred unit-dosage compositions are those containing a daily dose or sub-dose, as herein above recited, or an appropriate fraction thereof, of an active ingredient. Such pharmaceutical compositions may be prepared by any of the methods well-known in the pharmacy art.

There is thus further provided a pharmaceutical composition comprising a compound of formula (I), or a pharmaceutically acceptable salt thereof, and one or more pharmaceutically acceptable diluents or carriers.

There is also provided a process for preparing such a pharmaceutical composition which comprises admixing a compound of formula (I), or a pharmaceutically acceptable salt thereof, with one or more pharmaceutically acceptable diluents or carriers.

Throughout the description and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

Methods of preparing oxoadenine compounds and salts thereof are described in WO 2010/018134, the entire content of which is incorporated herein by reference. Methods for making compounds of formula (I), and for making 6-Amino-9-[5-(4-piperidinyl)pentyl]-2-[(1S)-1-methylbutyl]oxy]-7,9-dihydro-8H-purin-8-one, or a pharmaceutically acceptable salt thereof, are described herein and constitute a further aspect of this invention.

EXAMPLES

Example 1

Synthesis of Oxoadenines Substituted at the 9 Position

In the case of TLR7 and TLR8 activation, a few different classes of small molecule mimetics of the natural uridine- and/or guanosine-rich viral ssRNA ligands have been identified, including 1H-imidazo[4,5-c]quinolones, and 8-hydroxyadenines. See Heil, et al., *Eur.J.Immunol.* 2003, 33, 2987-2997; Hemmi, et al., *Nat Immunol* 2002, 3, 196-200; Lee, et al., *Proceedings of the National Academy of Sciences of the United States of America* 2006, 103, 1828-1833; Gerster, et al., *J.Med.Chem.* 2005, 48, 3481-3491; Hirota, et al., *J.Med.Chem.* 2002, 45, 5419-5422. Various evaluations of structure-activity relationships in oxoadenines have been done. See Isobe, et al., *Bioorganic & Medicinal Chemistry* 2003, 11, 3641-3647; Kurimoto, et al., *Bioorganic & Medicinal Chemistry* 2003, 11, 5501-5508; Kurimoto,et al., *Bioorganic & Medicinal Chemistry* 2004, 12, 1091-1099; Isobe,et al., *J.Med.Chem.* 2006, 49, 2088-2095; Jin, et al., *Bioorganic & Medicinal Chemistry Letters* 2006, 16, 4559-4563; Pryde, et al., R. *Med.Chem.Commun.* 2011, 2, 185-189; Kurimoto, et al., *J.Med.Chem.* 2010, 53, 2964-2972. Nakamura, et al., *Bioorganic & Medicinal Chemistry Letters* 2013, 23, 669-672; Weterings, et al., *Bioorganic & Medicinal Chemistry Letters* 2009, 19, 2249-2251.

The present inventors undertook a structure-activity relationship study on oxoadenines substituted with non-aromatic groups at the 9 position. Prior studies have examined a few 9-alkyl derivatives and suggested that the introduction of an alkyl (i-propyl, butyl, c-pentyl, c-hexyl) at the 9 position resulted in a weak and diminished activity (Hirota, et al., *J.Med.Chem.* 2002, 45, 5419-5422; Isobe, et al., *J.Med.Chem.* 2006, 49, 2088-2095). The present studies focused on the synthesis and biological evaluation of a series of seven oxoadenines of Formula I:

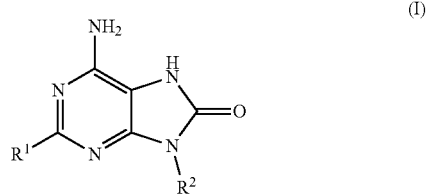

where $R^1$ is n-butoxy, and where $R^2$ is a piperidinylalkyl moiety in which the length of the carbon linker ranged from 0 to 6 carbons:

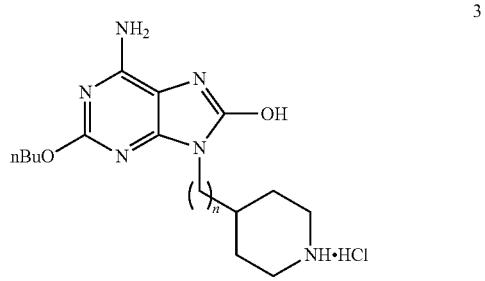

These compounds (3a-g) were evaluated in vitro for TLR7/8 selectivity and cytokine induction. Compound 3a has no carbon linker (n=0); 3b a one-carbon linker (n=1); 3c a two-carbon linker (n=2); 3d a three-carbon linker (n=3); 3e a four-carbon linker (n=4); 3f a five-carbon linker (n=5) and 3g a six-carbon linker (n=6).

The 9-piperidinylalkyl oxoadenines 3a-g were synthesized as outlined in Scheme 1 via the common advanced intermediate (CAI) 6. (Tanji et al., *Science* 2013, 339, 1426-1429.) CAI 6 was readily prepared on a multi-10 gm scale in 6 steps and in >50% overall yield starting from commercially available dichloropurine 7 (Scheme 2). In Scheme 2 Dichloropurine 7 was protected as the 9-tetrahydropyranyl derivative and substituted at the 6- position by treatment with 2M $NH_3$ in isopropanol at 60° C. to give the 2-chloro adenine 8 in 86% yield. Reaction of 8 with sodium tert-butoxide in n-butanol at 100° C. led to functionalized adenine 9 in 85% yield. The THP-protected adenine 9 was converted to CAI 6 in 3 steps and in 87% overall yield by 8-bromination, bromide displacement with methoxide, and THP-deprotection with trifluoroacetic acid (TFA). Alkylation of CAI 6 with the various tert-butyloxycarbonyl (Boc)-protected N-piperidinyl bromides 5b-g in the presence of potassium carbonate in dimethylformamide (DMF) followed by acidic deprotection of the Boc and methyl groups with 4N HCl in dioxane led to the desired oxoadenines 3b-g in 41-84% yields (Scheme 1). Alkylation of CAI 6 with bromide 5a failed and oxoadenine 3a was instead prepared in 38% yield by Mitsunobu reaction of CAI 6 with alcohol 4a in presence of DIAD and $PPh_3$ at 70 °C. followed by acidic deprotection (Scheme 1).

Scheme 1

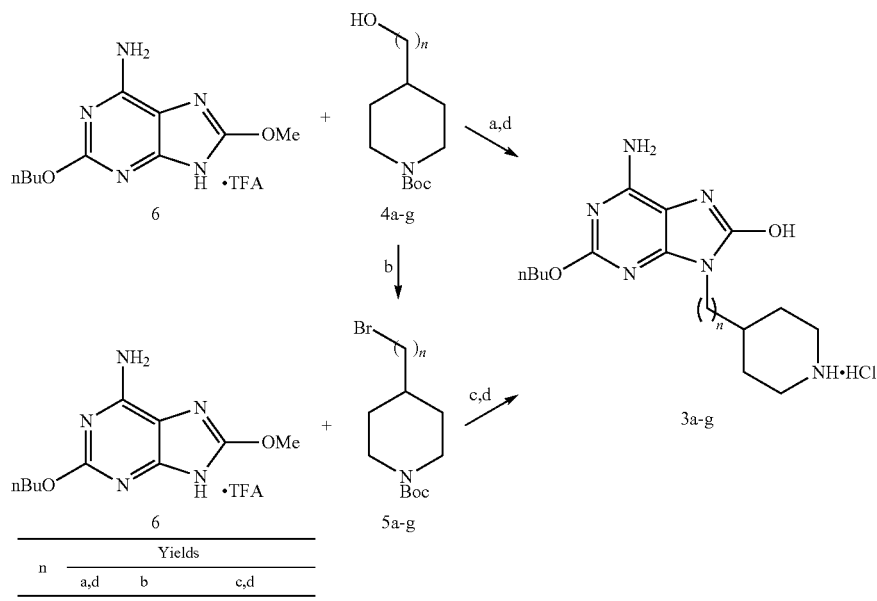

| n | Yields | | | | |
|---|---|---|---|---|---|
| | a,d | b | | c,d | |
| 0 | 38% | 5a | c.a. | 3a | NR |
| 1 | | 5b | 95% | 3b | 75% |
| 2 | | 5c | 94% | 3c | 83% |
| 3 | | 5d | 97% | 3d | 41% |
| 4 | | 5e | c.a. | 3e | 63% |
| 5 | | 5f | 92% | 3f | 64% |
| 6 | | 5g | 99% | 3g | 84% | c.a. commercially available; NR no reaction

Reagents: (a) TEA, PPh₃, DIAD, DMF, 70° C., 15 h; (b) CBr₄, PPh₃, CH₂Cl₂, RT, 1 h; (c) K₂CO₃, DMF, 50° C., 20 h; (d) 4N HCl/dioxane, MeOH, RT, 1 h;

Compound 3a had no carbon linker (n=0); 3b a one-carbon linker (n=1); 3c a two-carbon linker (n=2); 3d a three-carbon linker (n=3); 3e a four-carbon linker (n=4); 3f a five-carbon linker (n=5) and 3g a six-carbon linker (n=6).

Scheme 2: Synthesis of common advanced intermediate 6

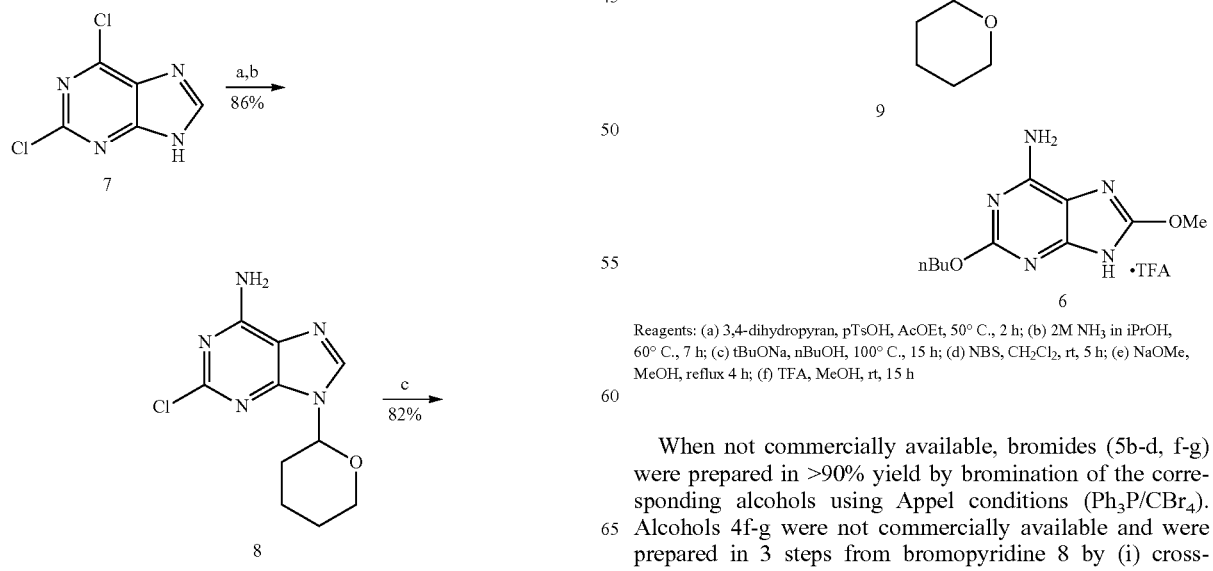

Reagents: (a) 3,4-dihydropyran, pTsOH, AcOEt, 50° C., 2 h; (b) 2M NH₃ in iPrOH, 60° C., 7 h; (c) tBuONa, nBuOH, 100° C., 15 h; (d) NBS, CH₂Cl₂, rt, 5 h; (e) NaOMe, MeOH, reflux 4 h; (f) TFA, MeOH, rt, 15 h When not commercially available, bromides (5b-d, f-g) were prepared in >90% yield by bromination of the corresponding alcohols using Appel conditions (Ph₃P/CBr₄). Alcohols 4f-g were not commercially available and were prepared in 3 steps from bromopyridine 8 by (i) cross-coupling of 10 with acetylenic alcohols 11f or 11g, (ii)

reduction of 12f and 12g with hydrogen in presence of 5% Rh/C catalyst and (iii) Boc protection of the amine group (Scheme 3):

Scheme 3: Synthesis of alcohols 4f and 4g

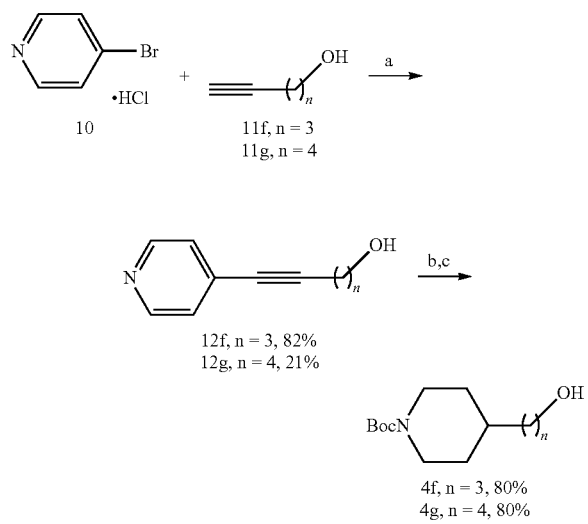

Reagents: (a) (PPh$_3$)PdCl$_2$, CuI, TEA, Δ, 30 min; (b) H-Cube, 5% Rh/C, H$_2$, AcOH, 90° C.; (c) BOC$_2$O, TEA, CH$_2$Cl$_2$, rt, 30 min.

Example 2

Synthesis of Oxoadenine Compound 3×

An additional oxoadenine (compound 3×) of Formula I was prepared, where:

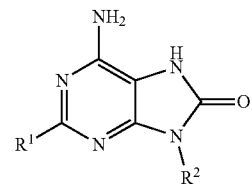

where R$^1$ is (1S)-1-methylbutoxy, and where R$^2$ is a piperidinylalkyl moiety in which the length of the carbon linker is 5 carbons. Compound 3×:

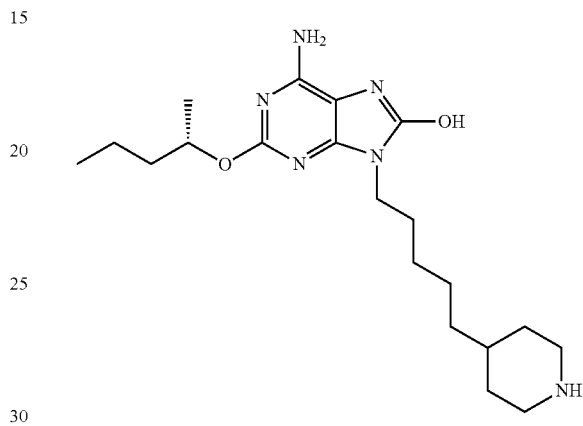

Oxoadenines and methods for preparing oxoadenines are also disclosed in WO2010/018134, the contents of which are incorporated herein in their entirety.

The synthesis of oxoadenine 3× was carried out according to Scheme 4 and as described below. Intermediate compounds 1, 2, 40, 41, 42 and 43 are additionally described in WO2010/018134 (the same numbering of these intermediates is used herein, as is used in WO2010/018134).

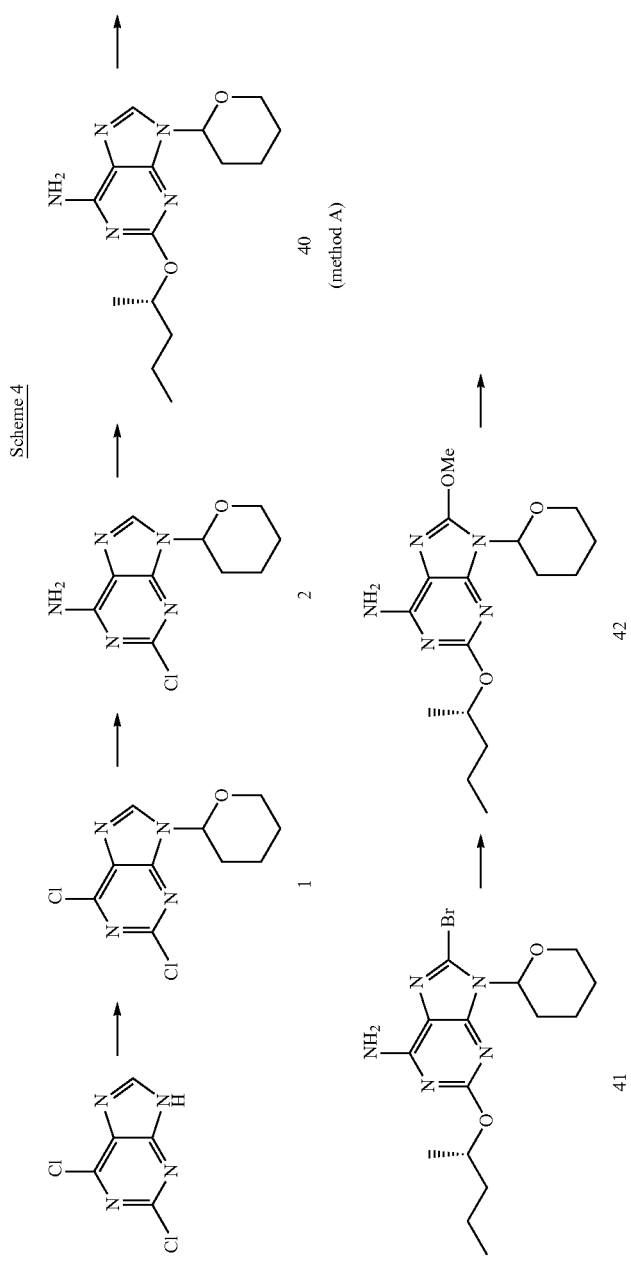
Scheme 4

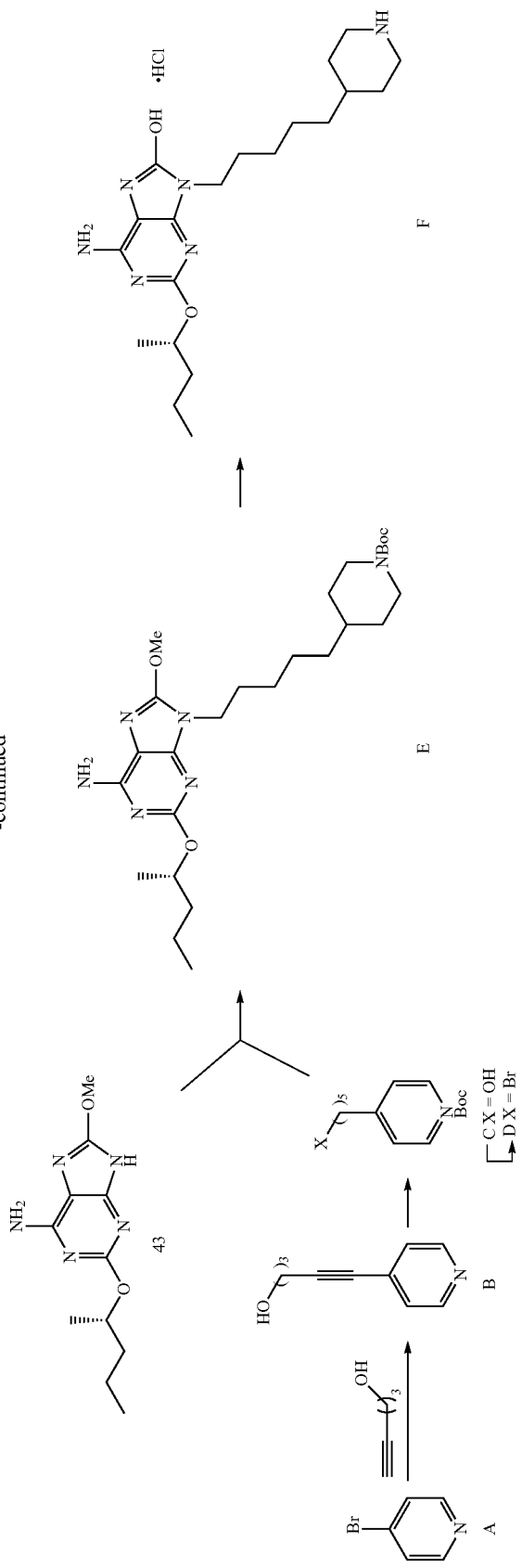

As shown in Scheme 4, 4-bromopyridine hydrochloride A (2.5 g) was partitioned between 1 N sodium hydroxide (20 ml) and ethyl acetate (3×20 ml). The organic layer was separated, dried over Na$_2$SO$_4$ and concentrated under vacuum. The resulting oil was dissolved in TEA (2.6 M) and degassed under nitrogen. 4-Pentyn-1-ol (1.1 eq) was added followed by bis(triphenylphosphine)palladium (II) chloride, (0.01 eq) and copper(I)iodide (0.02 eq) and the reaction mixture stirred at reflux for 20 min. Aqueous work-up (ethyl acetate/water) and purification by chromatography on silica gel (gradient 0-30% ethyl acetate in heptane) led to B in 82% yield. B was dissolved in acetic acid (0.05 M) and the solution hydrogenated using a H-CUBE® continuous-flow hydrogenation reactor (ThalesNano) (20% Pd(OH)$_2$/C cartridge, 100 bars H$_2$, 90° C., 1 mL/min).

Once the hydrogenation was complete, the reaction mixture was concentrated and dried under vacuum. The resulting crude was dissolved in CH$_2$Cl$_2$ (0.4 M), and reacted with Et$_3$N (1.5 eq) and di-t-buty dicarbonate (1.2 eq) at room temperature for 30 min. After aqueous work-up (CH$_2$Cl$_2$/H$_2$O) and purification by chromatography on silica gel (gradient 0-30% ethyl acetate in heptane) C was isolated in 80% yield: $^1$H NMR (400 MHz, CDCl$_3$) d 4.06 (s, 2H), 3.64 (t, 2H), 2.66 (t, 2H), 1.54-1.66 (m, 5H), 1.45 (s, 9H), 1.24-1.39 (m, 8H), 1.08 (m, 2H).

CBr$_4$ (1.6 eq) and PPh$_3$ (1.2 eq) were slowly added (exothermic reaction) to a solution of C in CH$_2$Cl$_2$ (0.45 M) at 0° C. After 5 minutes, the reaction mixture was allowed to warm up to room temperature, stirred at room temperature for 45 min, concentrated and directly purified by chromatography on silica gel (gradient 0-30% ethyl acetate in heptane) to give D in 92% yield.

K$_2$CO$_3$ (325 mesh, 3.0 eq) was added to a solution of 43 in DMF (0.25M) and the reaction mixture was sonicated several seconds to obtain a fine suspension then stirred at 60° C. for 1 h. After cooling to 50° C., D (1.2 eq) was added and the reaction mixture stirred overnight at 50° C. After cooling to room temperature and aqueous work-up (ethyl acetate/water) the resulting crude was purified by chromatography on silica gel (gradient 0-10% methanol in chloroform).

The purified product E was dissolved in methanol (0.1 M) and reacted with 4 N HCl in dioxane (6.0 eq) at room temperature for 1 h. The reaction mixture was concentrated and dried under vacuum and the residue purified by chromatography on silica gel (0-100% CHCl$_3$/CH$_3$OH/H$_2$O 90/10/0.5 in CHCl$_3$/CH$_3$OH/H$_2$O 85/15/1.0) to give F in 64% yield (2 steps). $^1$H NMR (400 MHz, CD$_3$OD) gamma 5.14 (m, 1H), 3.81 (t, 2H), 3.36/3.32 (m, 4H), 2.97(d of t, 2H), 1.92 (m, 2H), 1.75 (p, 2H), 1.72 (m, 1H), 1.57 (m, 2H) 1.5-1.3 (m, 14H), 0.95 (t, 3H); positive ES TOF-MS calc for [M+H]$^+$ 391.28222, found 391.0843.

Example 3

Preparation of Intermediates Shown in Scheme 4

Intermediate compounds 1, 2, 40, 41, 42 and 43 (see Scheme 4) are additionally described in WO2010/018134; the same numbering of these intermediates is used herein, as is used in WO2010/018134. LCMS Systems A-D are as described in WO2010/018134.

Intermediate 1: 2,6-Dichloro-9-(tetrahydro-2H-pyran-2-yl)-9H-purine

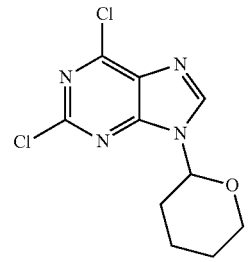 [SMILES: Clc1nc(Cl)c2ncn(C3CCCCO3)c2n1]

To 2,6-dichloropurine (25.0 g) (available from, for example, Aldrich, UK) was added ethyl acetate (260 mL), followed by p-toluenesulfonic acid (0.253 g). The mixture was heated to 50° C. and then 3,4-dihydro-2H-pyran (16.8 g) was added. The reaction mixture was then heated at 50° C. for 4 hours. The reaction mixture was evaporated in vacuo to give 2,6-Dichloro-9-(tetrahydro-2H-pyran-2-yl)-9H-purine as a yellow solid (36.9g).

$^1$H NMR (CDCl$_3$): δ 8.35 (1H, s), 5.77 (1H, dd), 4.20 (1H, m), 3.79 (1H, m), 2.20-1.65 (6H, m).

Intermediate 2: 2-Chloro-9-(tetrahydro-2H-pyran-2-yl)-9H-purin-6-amine

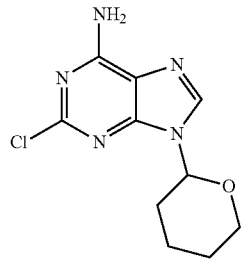 [SMILES: Nc1nc(Cl)nc2c1ncn2C1CCCCO1]

2,6-Dichloro-9-(tetrahydro-2H-pyran-2-yl)-9H-purine (36.9 g) was heated with 2M ammonia in isopropanol (250 mL) at 50° C. for 5 hours. After standing at ambient temperature overnight, a further quantity of 2M ammonia in isopropanol (100 mL) was added to break up the resultant cake and the reaction mixture was heated for a further 9 hours until the reaction was complete. To the reaction mixture was added water (70 mL) and the yellow solid filtered off. The solid was washed with isopropyl alcohol:water (5:1 (v/v), 60 mL) and then air-dried under suction to give a first crop. The filtrate was re-filtered after standing overnight to isolate precipitate and both solids were dried in vacuo. The first crop was pure with the second crop material showing a very minor impurity (isolated broad signal 3.5 ppm not seen in first crop) but was otherwise identical. Solid first crop (28.4g), solid second crop (3.42g).

$^1$H NMR (CDCl$_3$): 8.01 ($^1$H, s), 5.98 ($^2$H, broad s), 5.70 ($^1$H, dd), 4.16 ($^1$H, m), 3.78 ($^1$H, m), 2.15-1.60 ($^6$H, overlapping m).

Intermediate 2 (alternative method): 2-Chloro-9-(tetrahydro-2H-pyran-2-yl)-9H-purin-6-amine

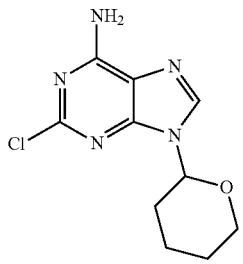 [SMILES: Nc1nc(Cl)nc2c1ncn2C1CCCCO1]

To a solution of 2,6-dichloropurine (25 g) (available from, for example, Aldrich, UK) in dry ethyl acetate (200 ml) was added p-toluenesulfonic acid monohydrate (235 mg). The reaction was heated to 50° C. and 3,4-dihydro-2H-pyran (18.1 ml) was added in one go. The reaction was allowed to stir at 50° C. for 1 hour and the solvent was removed under reduced pressure. This afforded a yellow solid. A suspension of this solid (~36 g) in 2.0M ammonia in isopropanol (460 ml) was heated under nitrogen at 60° C. for 4 hours with an attached condenser. The reaction was poured into water (50 ml) and left to cool overnight. The precipitate was filtered and dried on a rotary evaporator (60° C.) for 30 minutes to afford 2-chloro-9-(tetrahydro-2H-pyran-2-yl)-9H-purin-6-amine as an off-white solid, 31g (93%, 2 steps).

MS calculatedd for $(C_{10}H_{12}ClN_5O)^+$=254, 256
MS found (electrospray): $(M)^+$=254, 256 (3:1)
$^1H$ NMR $((CD_3)_2SO)$: δ 8.43 ($^1H$, s), 7.82 ($^2H$, s), 5.55 ($^1H$, dd), 4.00 ($^1H$, m), 3.69 ($^1H$, m), 2.21 ($^1H$, m), 1.95 ($^2H$, m), 1.74 ($^1H$, m), 1.56 ($^2H$, m).

Intermediate 40: 2-{[(1S)-1-Methylbutyl]oxy}-9-(tetrahydro-2H-pyran-2-yl)-9H-purin-6-amine

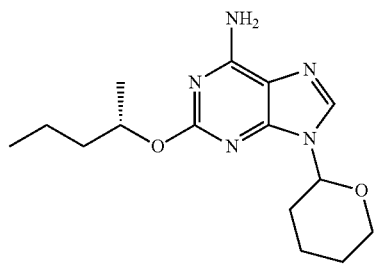 [SMILES: CCC[C@H](C)Oc1nc(N)c2ncn(C3CCCCO3)c2n1]

Method A:
Sodium t-butoxide (48.5g, 505mmol) was added portionwise to (S)-2-pentanol (185 ml) (available from, for example, Julich Chiral Solutions, Germany) at room temperature stirred until homogeneous (note reaction is exothermic). 2-Chloro-9-(tetrahydro-2H-pyran-2-yl)-9H-purin-6-amine (32g, 126mmol) was added and the reaction mixture heated at 70° C. for 72 hours. The reaction was cooled to room temperature and partitioned between ethyl acetate (500 ml) and water (500 ml).
The organic phase was washed with saturated sodium chloride solution (100 ml), dried (MgSO₄), filtered and evaporated. The residue was triturated with ether and the solid material filtered. The precipitate was re-washed with ether and the filtrates combined and evaporated. The crude material (ca. 30 g) was dissolved in DMSO:methanol (1:1) and purified by chromatography on a reverse-phase ($C_{18}$) column (330 g) using a gradient of 25-65% acetonitrile (+0.1%TFA)–water(+0.1%TFA) over 8 column volumes, the fractions were immediately neutralised with saturated aqueous sodium carbonate solution. Appropriate fractions were combined and partitioned between dichloromethane and saturated aqueous sodium hydrogen carbonate. The organic phase was dried by passage through a hydrophobic frit, filtered and evaporated to give 2-{[(1S)-1-methylbutyl]oxy}-9-(tetrahydro-2H-pyran-2-yl)-9H-purin-6-amine as a pale cream foam (14.97 g).

LCMS (System B): $t_{RET}$=2.21 min; $MH^+$ 306

Method B:
Sodium t-butoxide (206 g, 2.144 mol) was added to (S)-2-pentanol (720 ml, 6.58 mol) (available from, for example, Julich Chiral Solutions, Germany) in a 2 litre round bottomed flask. The mixture was stirred and 50° C. until all the sodium t-butoxide had dissolved. 2-Fluoro-9-(tetrahydro-2H-pyran-2-yl)-9H-purin-6-amine (130 g, 548 mmol) was then added in portions over 5 minutes.
After 3 hours LCMS analysis indicated complete consumption of the starting material and the mixture was poured into ice/water (3L) and then extracted with methyl t-butyl ether. This resulted in emulsion formation and the mixture was filtered through Celite and the organic phase was separated. The aqueous layer was then treated with solid NaCl and then re-extracted with methyl t-butyl ether. The organic extracts were combined and washed with brine, dried over magnesium sulfate, filtered and then evaporated to yield 2-{[(1S)-1-methylbutyl]oxy}-9-(tetrahydro-2H-pyran-2-yl)-9H-purin-6-amine as a pale brown gum (158.59 g).

LCMS (System D): $t_{RET}$ =2.65 min; $MH^+$ 306

Intermediate 41: 8-Bromo-2-{[(1S)-1-methylbutyl]oxy}-9-(tetrahydro-2H-pyran-2-yl)-9H-purin-6-amine

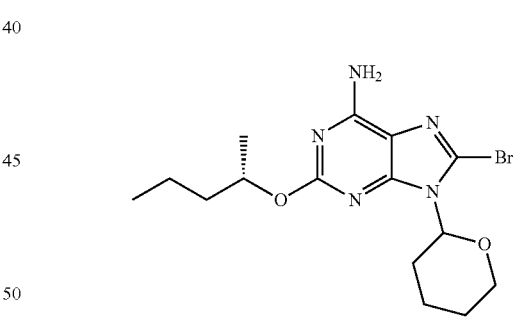

N-Bromosuccinimide (12.16 g, 68.3 mmol) was added portionwise over 5 mins. to a stirred solution of 2-{[(1S)-1-methylbutyl]oxy}-9-(tetrahydro-2H-pyran-2-yl)-9H-purin-6-amine (14.9 g, 48.8 mmol) in chloroform (80 ml) at <5° C. under an atmosphere of nitrogen. The reaction mixture was stirred at <5° C. for 5 hours then washed with saturated sodium hydrogen carbonate solution (80 ml) then water (80 ml). The foam was dissolved in DCM (50 ml) and washed with water (50 ml) then brine (50 ml). The combined aqueous phases were washed with DCM (50 ml). The combined organic layers were dried through a hydrophobic frit, and the solvent removed in vacuo to yield 8-bromo-2-{[(1S)-1-methylbutyl]oxy}-9-(tetrahydro-2H-pyran-2-yl)-9H-purin-6-amine as an orange foam (18.5 g).

LCMS (System D): $t_{RET}$=3.06min; $MH^+$ 384/386

Intermediate 42: 2-{[(1S)-1-methylbutyl]oxy}-8-(methyloxy)-9-(tetrahydro-2H-pyran-2-yl)-9H-purin-6-amine

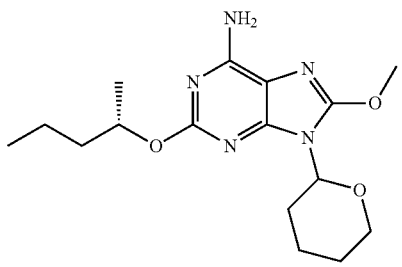 [SMILES: CCC[C@H](C)Oc1nc(N)c2nc(OC)n(C3CCCCO3)c2n1]

8-Bromo-2-{[(1S)-1-methylbutyl]oxy}-9-(tetrahydro-2H-pyran-2-yl)-9H-purin-6-amine (7.1 g, 18.48 mmol) was dissolved in anhydrous methanol (70 ml) and a solution of sodium methoxide (25%) in methanol (8 ml) was added dropwise under an atmosphere of nitrogen. The solution was heated to reflux at 90° C. for 4 hours under an atmosphere of nitrogen. Additional sodium methoxide in methanol (25% solution, 3m1) was added and the reaction was stirred at 60° C. for a further 16 hours. An additional portion of sodium methoxide in methanol (25% solution, 5m1) was added and the reaction was stirred at 90° C. for a further 7 hours. The solvent was removed on the rotary evaporator and the crude product was partitioned between EtOAc (75m1) and saturated ammonium chloride solution (75m1). The organic layer was washed with brine (75m1). The solvent was removed on the rotary evaporator to yield 2-{[(1S)-1-methylbutyl]oxy}-8-(methyloxy)-9-(tetrahydro-2H-pyran-2-yl)-9H-purin-6-amine as a pale orange foam (6 g).

LCMS (System D): $t_{RET}$=3.08 min; MH$^+$ 336

Intermediate 43: 2-{[(1S)-1-methylbutyl]oxy}-8-(methyloxy)-9H-purin-6-amine trifluoroacetate salt

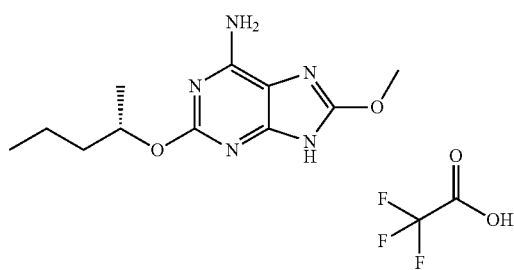 [SMILES: CCC[C@H](C)Oc1nc(N)c2nc(OC)[nH]c2n1 ; O=C(O)C(F)(F)F]

2-{[(1S)-1-methylbutyl]oxy}-8-(methyloxy)-9-(tetrahydro-2H-pyran-2-yl)-9H-purin-6-amine (6 g, 17.89 mmol1) was dissolved in methanol (50 ml). Trifluoroacetic acid (20.67 ml, 268 mmol) was added dropwise, and the mixture stirred at 2° C. for 72 hours under an atmosphere of nitrogen. The solvent was removed in vacuo, and the resulting solid was washed with ethyl acetate and filtered. The filtrate was stripped and the residue washed with ethyl acetate. The combined solid residues were dried in the vacuum oven for 2 hours to give 2-{[(1S)-1-methylbutyl]oxy}-8-(methyloxy)-9H-purin-6-amine trifluoroacetate salt as an off white solid (5.3 g).

LCMS (System C): $t_{RET}$=0.76 min; MH$^+$ 252

Preparation of additional compounds useful as intermediates in the production of oxoadenines, as well as preparation of additional oxoadenine compounds, is described in WO2010/018134, the entire content of which is incorporated herein by reference.

Example 4

Assay for the Induction of Interferon-alpha using Cryopreserved Human Peripheral Blood Mononuclear Cells (PBMCs)

The following method was used to test oxadenine compounds for in vitro biological activity.

Compound Preparation:

Compounds were dissolved in DMSO. Serial 2-fold dilutions with DMSO were prepared and 0.25 µl dispensed into 384-well clear Greiner polypropylene plates.

Preparation of PBMCs

Blood samples of up to 200 ml were obtained from healthy human donors. Whole blood in 25 ml volumes was overlaid onto 15 ml Ficoll gradients in Leucosep tubes, and centrifuged at 1000 g for 20 min. Cells in the band at the plasma/histopaque interface were carefully removed and washed twice with PBS (centrifuged at 400 g for 5 min to harvest). The final pellet was resuspended in freezing medium (90% Heat-inactivated serum, 10% DMSO) to a cell concentration of $4 \times 10^7$ cells/ml. The resuspended cells were then cryopreserved (frozen) using a rate controlled freezer, and stored at −140° C. for up to 4 months.

Incubation and Assay for Interferon-alpha

Immediately prior to assay, vials of cryopreserved (frozen) PBMCs were thawed rapidly in a water bath at 37° C. A 1:10 dilution of the cells in trypan blue was prepared and counted. The PBMCs were then diluted in growth media [RPMI 1640 containing 10% fetal calf serum (invitrogen), Penicillin+Streptavidin (Gibco cat. # 25030-024, 1:50), L-Glutamine 2mM, and 1000units/ml recombinant human IFN-gamma (Preprotech catalogue #300-02)] to a density of $1 \times 10^6$ cells/ml, and 50 ul/well dispensed to wells (in polypropylene plates) containing either 0.25 µl DMSO or test compound in 0.25 µl DMSO. Top final concentration of compound was typically 50 uM or 5 uM (to obtain curve fit for highly active compounds). Plates were incubated for 24 h at 37° C. in 5% $CO_2$.

A multi-isoform immunoassay was used to quantify IFN-alpha in PBMC supernatants. Rabbit polyclonal antibody against human IFN-alpha (catalogue number 31101, Stratech Scientific) was diluted 1:10000 in assay buffer (RPMI 1640 containing 10% fetal calf serum, Invitrogen) and 20 µl was added to each well of an MSD (Meso-Scale Discovery, Gaithersburg, Md., USA) single small-spot GAR (goat anti-rabbit antibody coated) well plate. The plate was incubated for 1 hour at room temperature with vigorous shaking. Following three washes with PBS, 20 µl of cell supernatant were added to each well of the plate. The plate was then incubated for 1 hour at room temperature with vigorous shaking. A pair of monoclonal antibodies to IFN- alpha (catalogue numbers 21100 and 21112, Stratech Scientific) were labelled with SULFO-TAG (™) (MSD), diluted 1:1000 in assay buffer and 20 µl added to each well of the plate. The plate was further incubated for 1 hour at room temperature with vigorous shaking. Following three washes with PBS, 30 µl of x2 T buffer (MSD) was added to each well and the plate was read on an MSD Sector 6000 plate reader.

Data were normalised to internal plate controls of 1 uM resiquimod (n=16) and DMSO (n=16). pEC50 values were derived by 4-parameter curve fit with IRLS (iteratively reweighted least squares) in ActivityBase software, from 11-point, two-fold serial dilution of test compounds.

Example 5

Assay for the Induction of Interferon-alpha and TNF-alpha using Fresh Human Peripheral Blood Mononuclear Cells (PBMCs)

Compound Preparation

Compounds were dissolved in 2% glycerol in water to working concentrations starting at 10 µM, serially diluted to 0.00013 µM with 5-fold dilutions. This compound preparation was added to 96-well flat bottom plates at a volume of 10 µl.

An additional 10 µl of media was added to these wells, or another compound preparation if co-stimulation was intended.

Preparation of PBMCs

Blood samples from human donors were collected into heparinized 60 cc syringes, and divided into 20 ml aliquots in 50 ml conical culture tubes. The whole blood aliquots were then diluted with 15 ml of PBS, and then underlayed with 15 ml HISTOPAQUE(™). The samples were centrifuged at 800 g for 30min with no brake and the buffy coat interface carefully removed. The collected cells were centrifuged at 1500 rpm for 5 minutes and the pellet resuspended in 10 ml of PBS. The cells were pooled and further washed twice in PBS to remove all HISTOPAQUE(™) from the samples. After the final wash, the combined cells were brought up in 20 ml complete media (RPMI 1640 supplemented with 10% v/v heat-inactivated Fetal Bovine Serum (FBS), 100 U/ml penicillin G, 100 µg/ml streptomycin, 10 mM L-glutamine), counted using a Countess automated cell counter (Invitrogen, Life Technologies) and diluted to give a final concentration of $2.8 \times 10^6$/ml. This cell suspension was added to the culture plate containing the compound preparations (see above), at a volume of 180 µl, resulting in a total well volume of 200 µl.

Incubation and Assays for Interferon-alpha and TNF-alpha

After 24 hr incubation (37° C., 95% air, 5% $CO_2$), the supernatants were carefully removed and assayed for cytokine/chemokine induction using multiplex kits (FLUOROKINE(™) multiplex kits from R&D Systems [biotechne], Minneapolis, Minn.) and human IFNα VERIKINE(™) ELISA kit (Pestka Biomedical Laboratories, Inc., Piscataway, N.J).

Example 6

Allergen-driven Cytokine Assay using Fresh Human Peripheral Blood Mononuclear Cells (PBMCs) from Atopic Volunteers An assay based on co-culture of atopic human donor derived peripheral blood mononuclear cells (PBMCs) with allergen and test compounds was developed. After 5-6 days culture, cell supernatants were assayed for a range of cytokines.

Compound Preparation

Compounds were dissolved in DMSO, then serially diluted in growth medium (RPMI 1640 medium supplemented with 100 U/ml penicillin G, 100 µg/ml streptomycin, 10 mM L-glutamine) to give 4× the required concentration range in the presence of 0.04% DMSO. Each compound was assayed in triplicate at all concentrations.

Preparation of PBMCs

Defibrinated human blood from volunteers known to be allergic to Timothy grass was centrifuged at 2500 rpm for 15 minutes. The upper layer of serum was collected and heat-inactivated at 56° C. for 30 minutes (HI-autologous serum). The lower layer of cells was resuspended in 50ml PBS (+Ca +Mg), 25ml diluted blood were overlaid onto 20 ml LYMPHOPREP(™) in 50 ml tubes then centrifuged at 2500 rpm for 20 minutes at RT. The band at the serum/LYMPHOPREP (™) interface was carefully removed. The collected cells were washed with PBS and re-suspended at $4 \times 10^6$/ml in growth medium with HI-autologous serum. PBMCs were seeded at $0.4 \times 10^6$ cells /well in flat-bottomed 96 well plates in the presence of 10 µg/ml Timothy grass antigen (Alk-Abello, Denmark) and test compounds at appropriate concentrations in a total volume of 200 µl.

Incubation and Cytokine Assays

Plates were incubated at 37° C. in 5% $CO_2$ for up to 6 days. The cell medium from each well was harvested and stored at −20° C. prior to analysis. Cytokines and chemokines in supernatants were detected using MESO SCALE DISCOVERY™ 10 spot plates for Human TH1/Th2 cytokines.

Example 7

TLR7/8 Activity of Oxoadenines 3a-3g

The human (h) TLR7/8 activity of oxoadenines 3a-g was assessed by a reporter gene assay using HEK293 cells stably transfected with either hTLR7 or hTLR8, and with the NFKB SEAP (secreted embryonic alkaline phosphatase) reporter.

HEK293 cells expressing human TLR7 or TLR8, and NFKB responsive SEAP reporter gene, were obtained from InvivoGen (San Diego, Calif.). These cells were maintained in culture media of Dulbecco's Modified Eagle Medium (DMEM) (Invitrogen, Grand Island, N.Y.), 10% Fetal Bovine Serum (FBS) (Sigma, St. Louis, Mo.) and selection antibiotics (Invitrogen and InvivoGen). The stably transfected HEK293 cells were plated in 96-well flat bottom culture plates at $1^{E5}$/well and stimulated for 24 h with a dose range of aqueous formulations of compounds starting at 200 µM serially diluted to 0.012 µM with 2-fold dilutions (unless formulation conditions warranted lower starting concentrations). Culture supernatants were harvested and assayed for NFκB activation using the colorimetric SEAP detection kit QUANTI-BLUE (a trademark of InvivoGen).

Figure 1B:
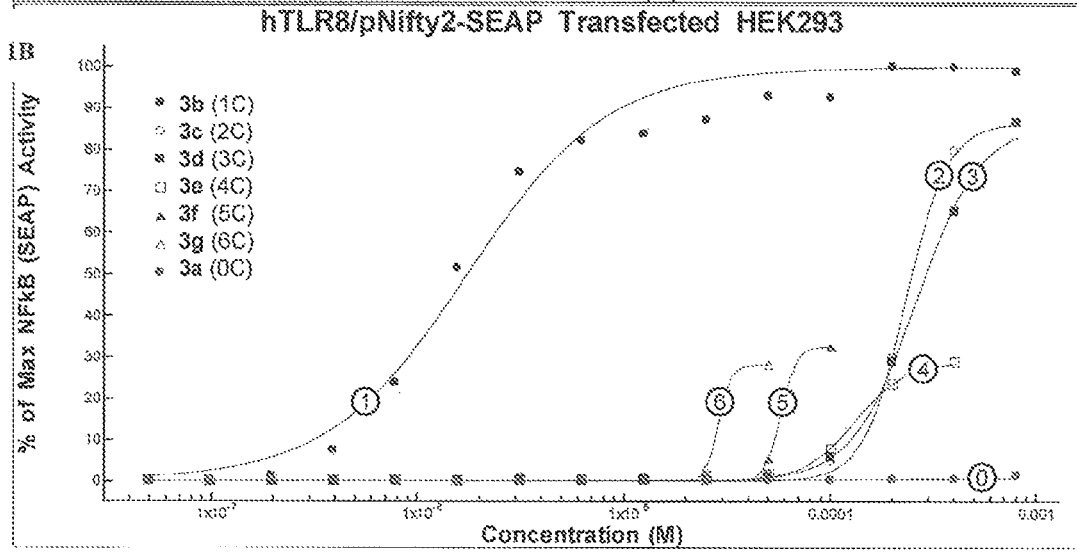

The assay measured NFκB mediated SEAP production following TLR7 or TLR8 specific activation. The hTLR7 and hTLR8 specificity and potency ($EC_{50}$) of oxoadenines 3a-g are shown in FIGS. 1A-C.

It should be noted that the HEK assay is not optimal for evaluating TLR7 since TLR7 signals via both the NFκB (leading to induction of inflammatory cytokines) and IRF7 pathways (leading to IFN induction) and the HEK system only measures the NFκB side of TLR7 signaling. Oxoadenine 3a was not active on hTLR7 or hTLR8 but the other oxoadenines 3b-g were all active. While increasing the linker length beyond 1 carbon increased hTLR7 potency, no linear correlation between carbon linker length and hTLR7 potency was observed in this assay. The 5-carbon linker oxoadenine 3f was the most potent hTLR7 agonist of the series (see FIG. 1C) while the 1-carbon linker oxoadenine 3b was the most potent hTLR8 agonist of the series with hTLR8 potency significantly decreased with longer carbon linkers.

The loss of hTLR8 activity observed after stimulation with higher doses of oxoadenines 3e-g suggested possible cell toxicity in HEK293-hTLR8 cells. LIVE/DEAD(™) fixable Aqua staining was used to evaluate potential cell death following HEK293-hTLR8 stimulation with oxoadenines 3e-g. Significant cell toxicity was observed at higher doses of oxoadenines 3e-g (data not shown). This cell toxicity was not observed after 24 hours stimulation with the shorter carbon linker oxoadenines 3b-d (data not shown).

Figure 2A:
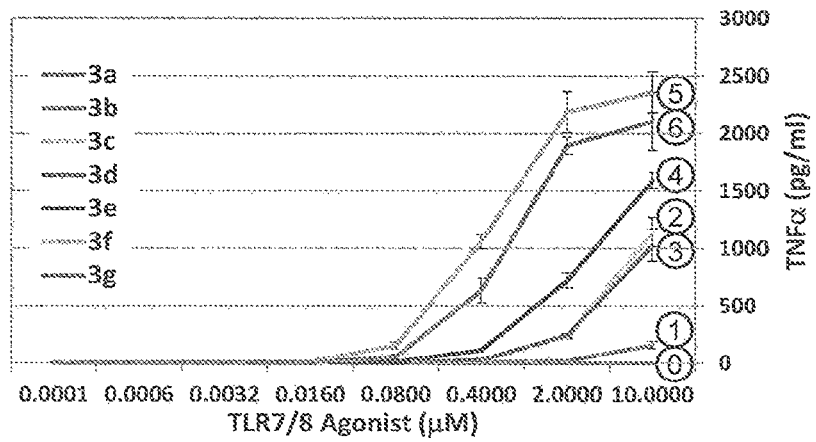
FIG. 2 (A) shows TNFalpha induction in hPBMCs and (B) IL-6 expression in mDC after stimulation with oxoadenine compounds 3a-g. The experiment was done in triplicate in hPBMCs from three different healthy donors. Circled numbers indicate the carbon linker length of each compound.
Figure 2B:
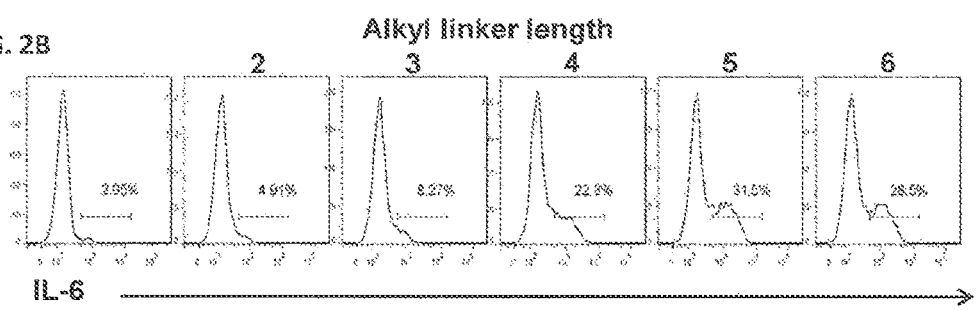

The induction of cytokines in human peripheral blood mononuclear cells (hPBMCs) after 24 hours stimulation with oxoadenines 3e-g was next evaluated using cytokine ELISA and intracellular cytokine staining (ICS). Induction of TNFα is shown in FIG. 2A. A clear increase in TNFα secretion with increasing carbon-length was observed, with maximal TNFα secretion observed for the five carbon linker.

ICS was also used to examine the activation status and cytokine contributions of distinct cell subsets. A similar pattern was observed in Myeloid Dendritic cells (mDCs) when comparing IL-6 (FIG. 2B), TNFα and IFNγ induction. Taken together, these data strongly suggest an increase of proinflammatory cytokines as the carbon linker increases to five carbons. The 6-carbon linker oxoadenine 3g induced less TNFα than 3f but more than the 4-carbon linker oxoadenine 3e.

Figure 3:
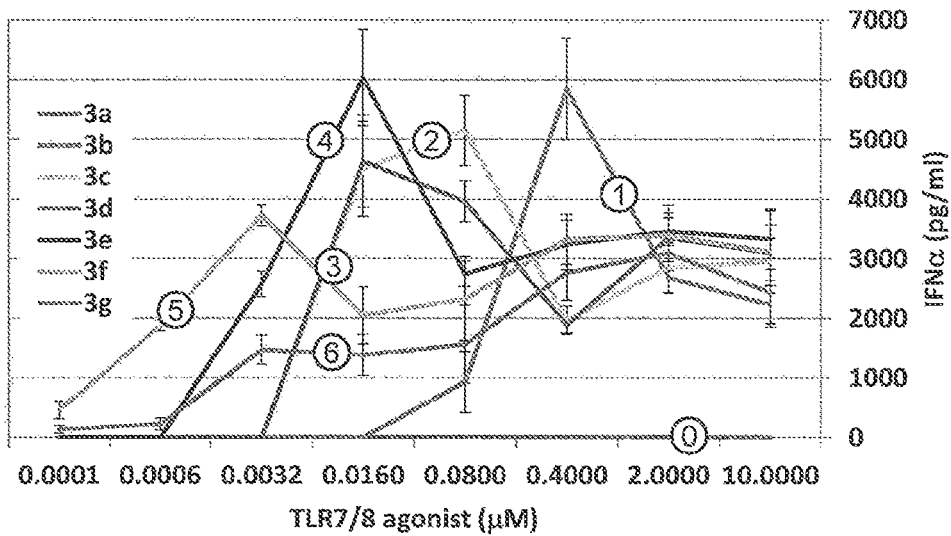
FIG. 3 graphs IFNalpha induction in hPBMCs after stimulation with oxoadenines 3a-g.

The induction of IFNα from hPBMCs upon stimulation with oxoadenines 3a-g was also evaluated. Given the non-linear relationship observed between the carbon linker length and the hTLR7 $ED_{50}$ values obtained with oxoadenines 3a-g in the HEK293 system (which is indicative of the NFκB side of TLR7 signaling), IFNα induction from hPBMCs was expected to be more representative of the hTLR7 activity of these compounds. A unique pattern for IFNα expression was observed for compounds 3a-g (FIG. 3).

Each of compounds 3a-g exhibited a bell shaped dose response curve from peak to base within a 100 μM dose range, except oxoadenine 3a, which was inactive. Oxoadenines with increasing carbon linker length were increasingly more potent IFNα inducer, as indicated by the lower dose required to achieve maximum IFNα response, but higher concentrations of oxoadenines were associated with a dose responsive decrease in IFNα. Concurrently, TNFα levels in the same cell culture supernatants increased in a dose-dependent fashion. pDC is the primary cell type responsible for >90% of IFNα secretion, therefore suppression of the TLR7-IRF7 signaling pathway via a regulatory feedback loop to restrict the activation magnitude of IFNα or cell-type specific activation induced cell death (AICD) might be responsible for the unique cytokine pattern observed in this study.

To evaluate these hypotheses, hPBMCs were stimulated with various doses of 3b (1-carbon linker) or 3f (5-carbon linker) and the cells were evaluated for activation induced apoptosis by Annexin-V staining. 3f was associated with a dose dependent increase in Annexin-V staining in pDC but not in mDC. In contrast, only the highest dose of 3b (10 mM,) was associated with Annexin-V positive cells in both pDC and mDC subsets. This observed cell type specific apoptosis correlated with the dose-dependent IFNα and TNFα induction curves.

To further confirm the effect of pDC apoptosis upon IFNα induction, co-stimulation with equimolar amounts of 3b and 3f was evaluated in hPBMCs. As expected, the combination of a high dose (~0.3 μM) of 3f and 3b reduced the IFNα peak as compared to 3b alone, whereas the combination of a lower dose of 3f and 3b (~0.003 μM) did not alter the IFNα peak response by 3f alone (data not shown). Overall, these results demonstrate that increasing the carbon linker from 1 to 5 carbons increases the potency for IFNα induction from pDC but also reduces the dose threshold for apoptosis while leaving TNFα induction from mDC largely unaltered.

In summary, the structure-activity relationship of seven oxoadenines (3a-3g) substituted at the 9 position with a piperidinyl alkyl moiety was investigated. A minimum of 1-carbon linker was required for hTLR7 and hTLR8 activity. The 5-carbon linker oxoadenine was the most potent hTLR7 agonist while the 1-carbon linker was the most potent hTLR8 agonist of the series. Proinflammatory cytokines and IFNα induction in hPBMCs increased with increasing carbon length up to 5 carbons, with the 5-carbon linker oxoadenine being the most potent cytokine inducer. These results indicate that it is possible to modulate hTLR7/8 activity and cytokine induction in the oxoadenine series with non-aromatic groups at N-9 using minor structural modification.

Example 8

TLR7 and TLR8 Specificity and Potency of Compound 3x

Compound 3x is shown to have improved TLR7potency and TLR7-bias agonist activity compared to other oxoadenines investigated.

Figure 4A:
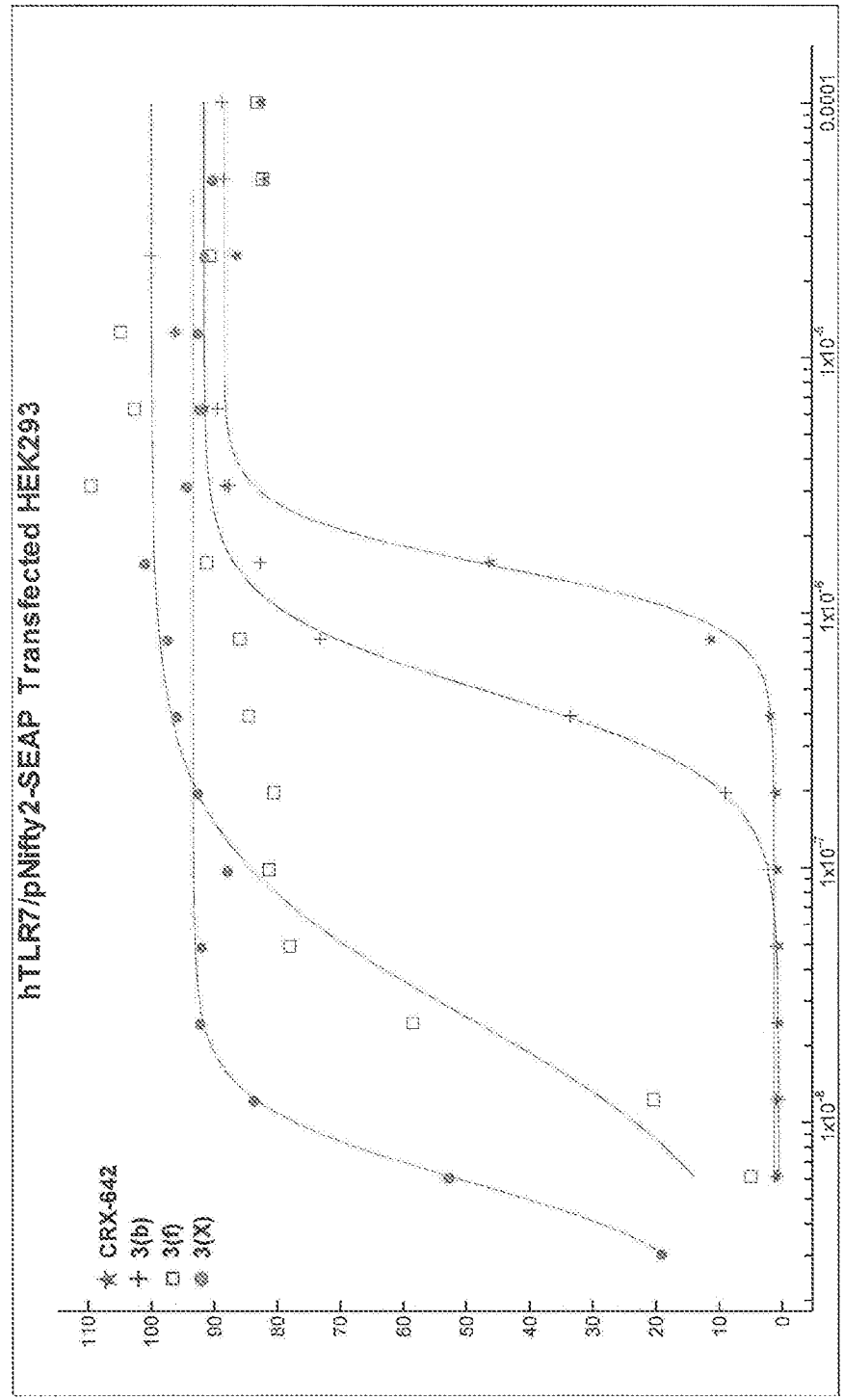
FIG. 4 graphs NFkB response from (A) HEK293-hTLR7 and (B) HEK293-hTLR8 cells treated for 24 hours with oxoadenine compounds 3b, 3f, or 3x, or imidazoquinoline CRX642.
Figure 4B:
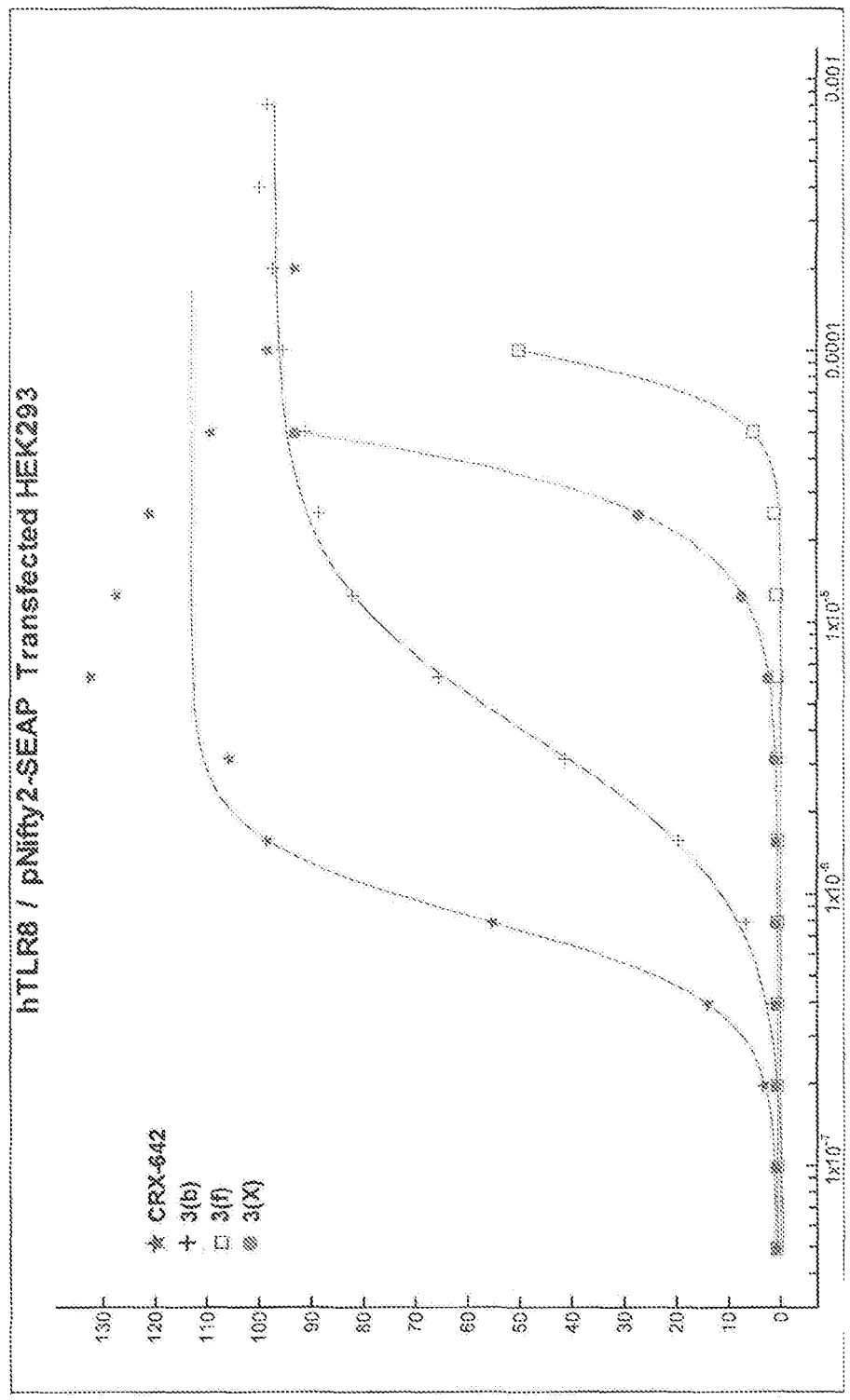

In relation to oxoadenine 3b, compounds 3f and 3x had 50- and 100-fold higher TLR7 potency, respectively (FIG. 4A), and lower TLR8 activity (FIG. 4B). The influence of the C2 substituent can be seen by comparing 3f and 3x: introducing a (S)-methyl group on the first carbon of the C2-butoxy chain increased both TLR7 and TLR8 activity.

Figure 5:
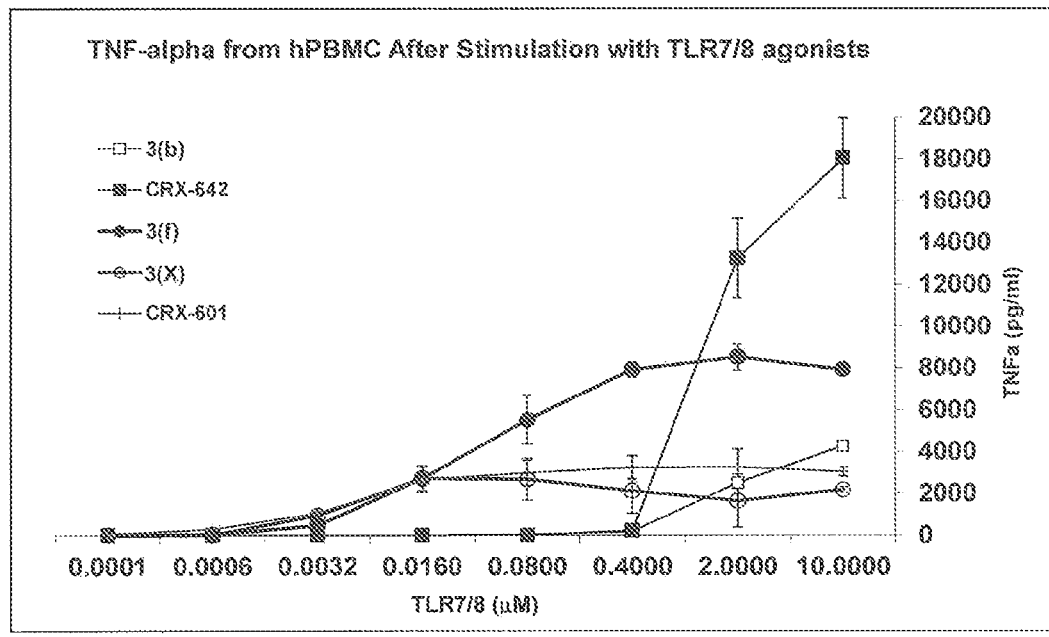
FIG. 5 graphs TNFalpha induction from human PBMCs by stimulation with different oxoadenine compounds (3b, 3f or 3x), or imidazoquinoline CRX642, or AGP compound CRX601.

When evaluated for cytokine induction in hPBMCs, compound 3f and 3x displayed high potency (lower $ED_{50}$) and TNF-alpha response (FIG. 5). The same result was observed for other pro-inflammatory cytokines (data not shown).

Figure 6:
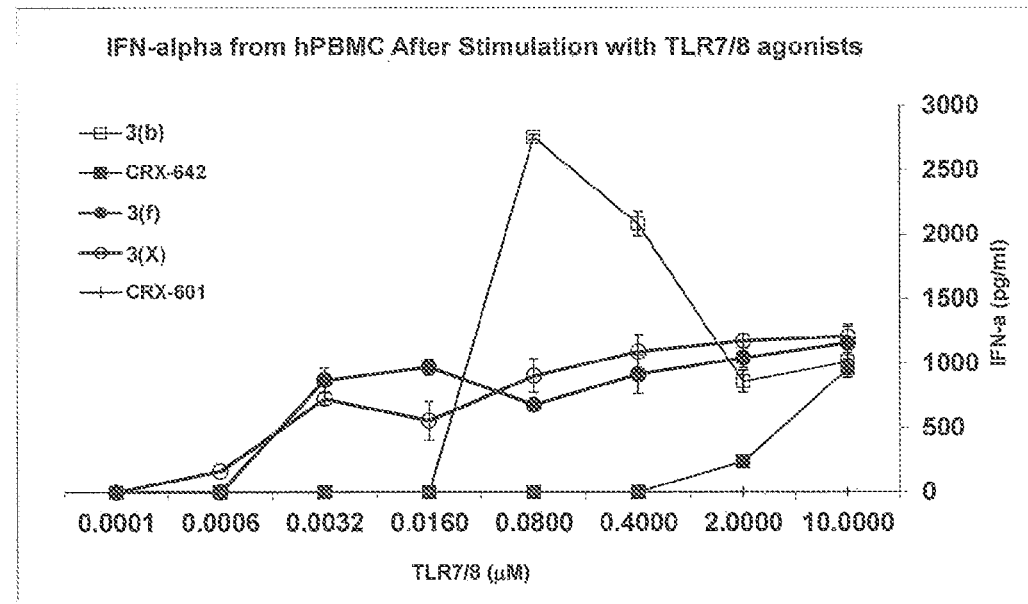
FIG. 6 graphs IFN-alpha induction in human PBMCs by stimulation with different oxoadenine compounds (3b, 3f or 3x) or AGP CRX601 or CRX642 (imidazoquinaline).

As expected based on the low TLR7 $ED_{50}$ seen in the HEK293 assay for compound 3f and 3x, both oxoadenines induced IFN-alpha at very low doses (~1nM range) (FIG. 6).

Figure 7:
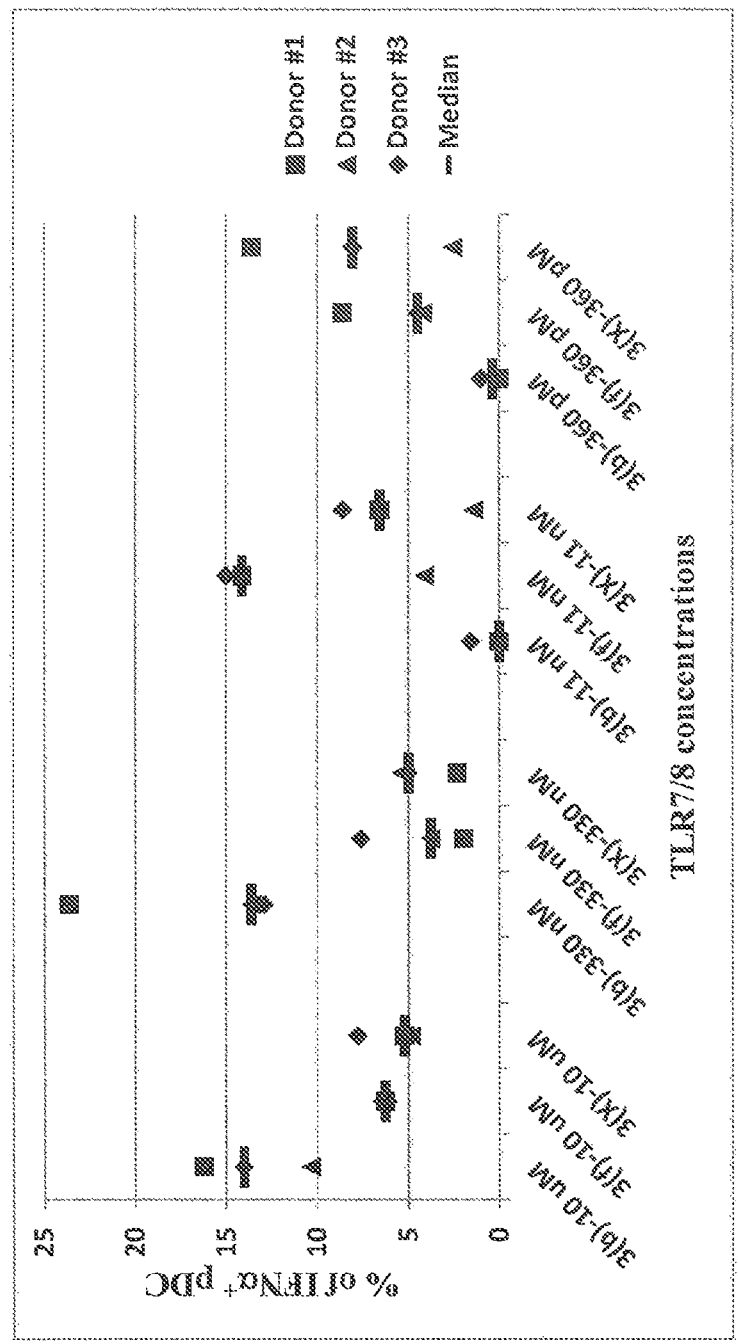
FIG. 7 shows IFNalpha induction in pDC from three different donors, as measured by ICS (Intracellular Cytokine Staining), by stimulation with different oxoadenines (3b, 3f or 3x), at different dosages.

FIG. 7 shows IFN-alpha induction by oxoadenines as measured by ICS. Cytokine induction was analyzed by percent of total live pDC cells positive for IFN-alpha. Dosages used were 360 picomolar, 11 nanomolar, 330 nanomolar and 10 micromolar.

Figure 8A:
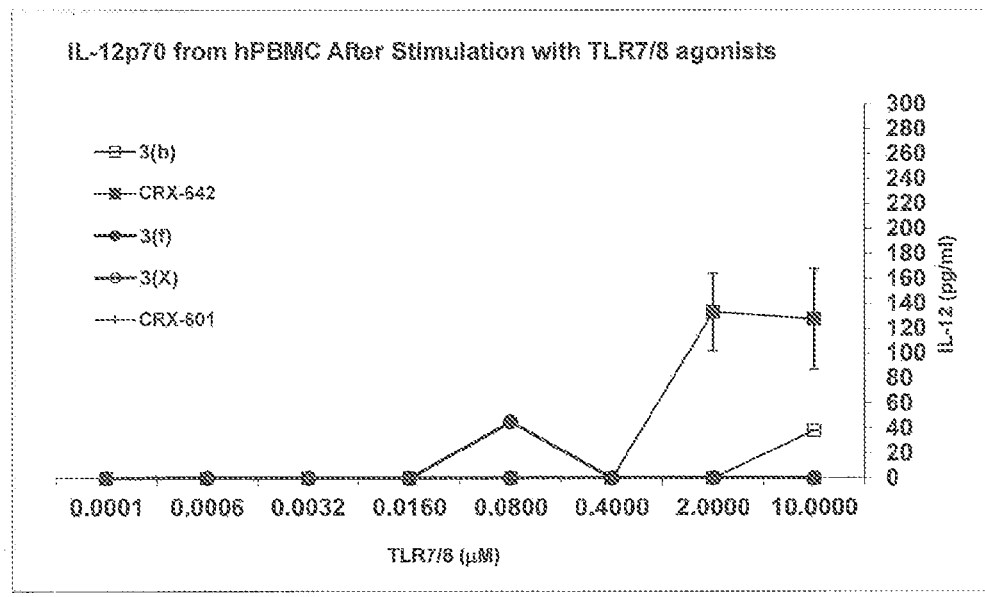
FIG. 8A graphs IL-12p70 induction in human PBMCs by different oxoadenines (3b, 3f, or 3x) or AGP CRX601 (TLR4 agonist) or CRX642 (imidazoquinaline).
Figure 8B:
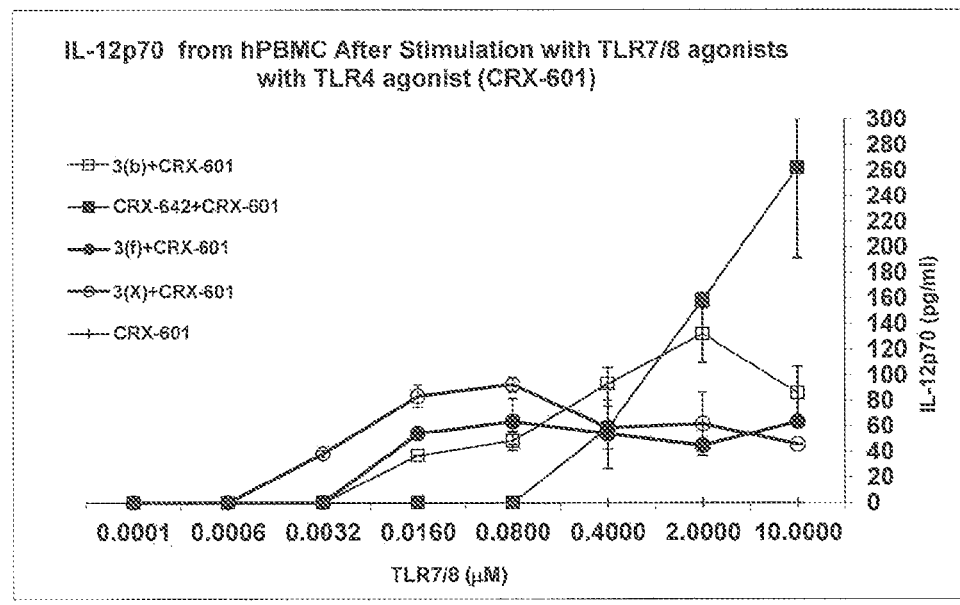
FIG. 8B graphs IL-12p70 induction in human PBMCs by different oxoadenines (3b, 3f, or 3x) in combination with CRX601 (TLR4 agonist), or CRX642 (imidazoquinaline) in combination with CRX601.
Figure 9:
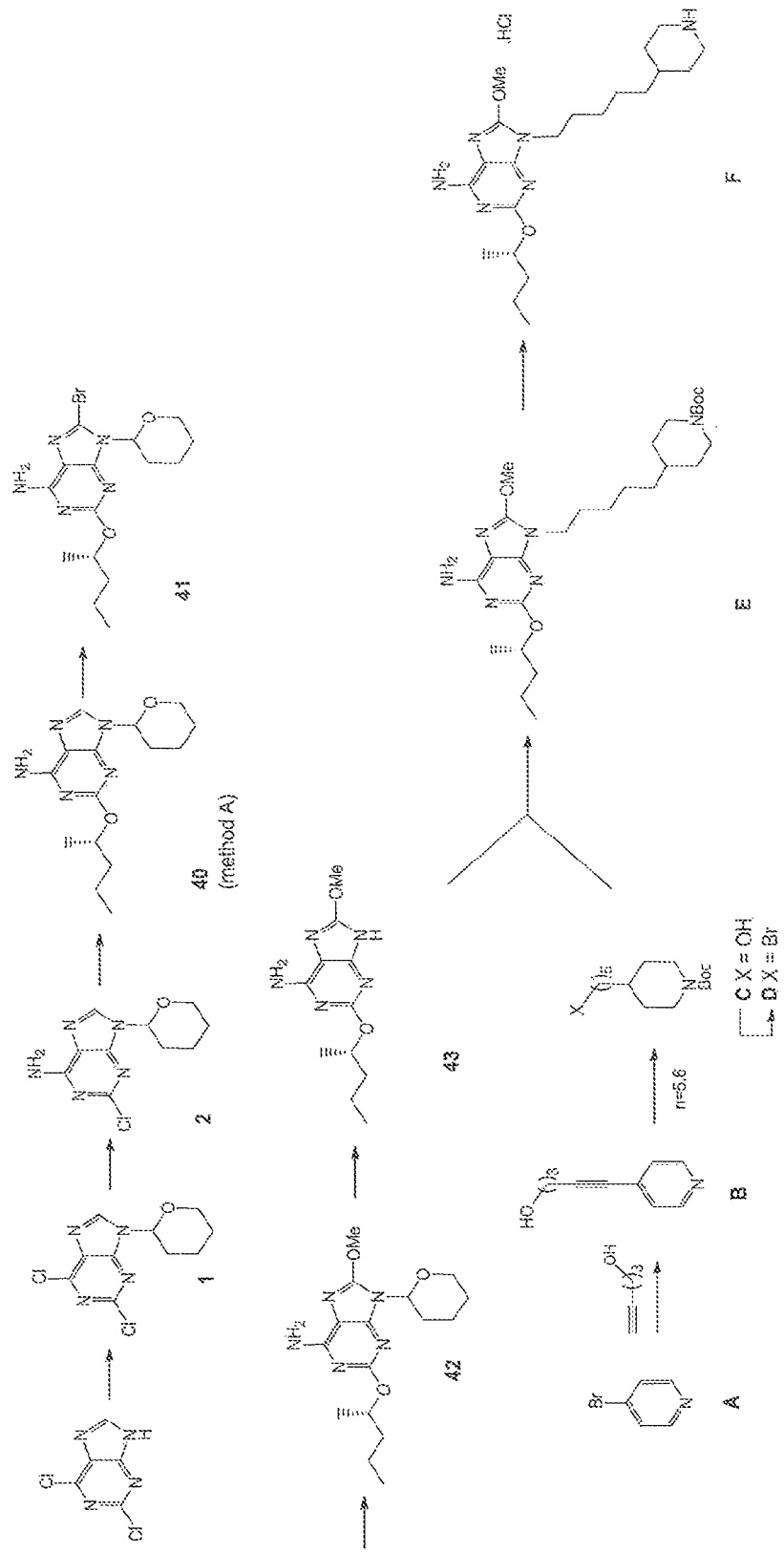
FIG. 9 is Scheme I showing the synthesis of oxoadenine compound 3x, a compound according to formula (I).

As previously observed with other oxoadenines (see WO2010/018134), synergy with AGP CRX601 for IL12-p70 was relatively low compared to imidazoquinoline compound CRX642 (see WO2010/048520; PCT/US2009/061867; U.S. Pat. No. 8,624,029) in combination with CRX601. However, compound 3x and 3f demonstrated synergy with CRX601 throughout a wide dose range (FIG. 8A and 8B).

Table 2 summarizes the data discussed above. Notice compound 3x for its low TLR7 $ED_{50}$ and high relative IFN-alpha and IL-12p70 induction.

TABLE 2

| | HEK 293 | | | PBMC/Monocytes | | |
|---|---|---|---|---|---|---|
| | TLR7 ED$_{50}$ (μM) | TLR8 ED$_{50}$ (μM) | Ratio TLR 7/8 | IL-12p70 w/601 | IFNα | Infl. Cytok. |
| 3f | 0.026 | 99.85 | 3E−04 | ** | */**** | *** |
| 3x | 0.006 | 93.97 | 1E−04 | ** | */**** | */*** |

\* through \*\*\*\*: lowest to highest cytokine induction level;

The invention claimed is:

1. A compound of formula (I):

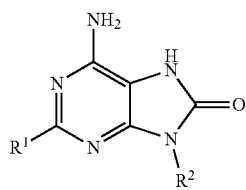

wherein;
R$^1$ is methylbutoxy;
R$^2$ is a group having the structure:

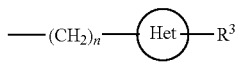

where n is an integer having a value of five;
Het is a six-membered saturated heterocycle containing five carbon atoms and one nitrogen atom, wherein Het is attached to the —(CH$_2$)$_n$— moiety at the carbon 4 position of the heterocycle; and
R$^3$ is hydrogen;
or a pharmaceutically acceptable salt thereof.

2. The compound 6-amino-9-[5-(4-piperidinyl)pentyl]-2-[(1S)-1-methylbutyl]oxy]-7,9-dihydro-8H-purin-8-one:

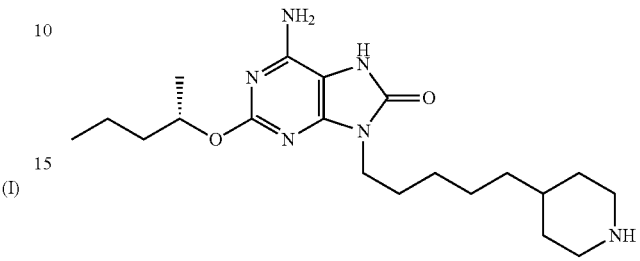

or a pharmaceutically acceptable salt thereof.

3. A pharmaceutical composition comprising a compound as defined in claim 1, and one or more pharmaceutically acceptable diluents or carriers.

4. A composition comprising a compound as defined in claim 1, and further comprising a component selected from: (a) at least one other therapeutically active agent, (b) a pharmaceutically acceptable diluents, and (c) a pharmaceutically acceptable carrier.

5. The compound of claim 3, wherein the compound is 6-amino-9-[5-(4-piperidinyl)pentyl]-2-[(1S)-1-methylbutyl]oxy]-7,9-dihydro-8H-purin-8-one.

6. The compound of claim 3, wherein the compound is a pharmaceutically acceptable salt of 6-amino-9-[5-(4-piperidinyl)pentyl]-2-[(1S)-1-methylbutyl]oxy]-7,9-dihydro-8H-purin-8-one.

* * * * *

UNITED STATES PATENT AND TRADEMARK OFFICE
CERTIFICATE OF CORRECTION

| | |
|---|---|
| PATENT NO. | : 10,584,125 B2 |
| APPLICATION NO. | : 15/526345 |
| DATED | : March 10, 2020 |
| INVENTOR(S) | : Bazin-Lee et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 201 days.

Signed and Sealed this
Nineteenth Day of December, 2023

Katherine Kelly Vidal
*Director of the United States Patent and Trademark Office*